US008401618B2

(12) United States Patent
Lorenzo et al.

(10) Patent No.: US 8,401,618 B2
(45) Date of Patent: *Mar. 19, 2013

(54) SYSTEMS AND METHODS FOR TOMOGRAPHIC IMAGING IN DIFFUSE MEDIA USING A HYBRID INVERSION TECHNIQUE

(75) Inventors: Jorge Ripoll Lorenzo, Madrid (ES); Wael I. Yared, Lexington, MA (US); Joshua Kempner, Reading, MA (US)

(73) Assignee: VisEn Medical, Inc., Woburn, MA (US)

( * ) Notice: Subject to any disclaimer, the term of this patent is extended or adjusted under 35 U.S.C. 154(b) by 196 days.

This patent is subject to a terminal disclaimer.

(21) Appl. No.: 12/870,454

(22) Filed: Aug. 27, 2010

(65) Prior Publication Data

US 2011/0060211 A1    Mar. 10, 2011

Related U.S. Application Data

(60) Provisional application No. 61/238,075, filed on Aug. 28, 2009.

(51) Int. Cl.
  *A61B 5/05* (2006.01)
(52) U.S. Cl. ........................................... 600/425
(58) Field of Classification Search .................. 600/476
  See application file for complete search history.

(56) References Cited

U.S. PATENT DOCUMENTS

| 4,981,977 | A | 1/1991 | Southwick et al. |
| 5,268,486 | A | 12/1993 | Waggoner et al. |
| 5,486,616 | A | 1/1996 | Waggoner et al. |
| 5,569,587 | A | 10/1996 | Waggoner |
| 5,569,766 | A | 10/1996 | Waggoner et al. |
| 5,627,027 | A | 5/1997 | Waggoner |
| 5,808,044 | A | 9/1998 | Brush et al. |
| 5,877,310 | A | 3/1999 | Reddington et al. |
| 6,002,003 | A | 12/1999 | Shen et al. |
| 6,004,536 | A | 12/1999 | Leung et al. |
| 6,008,373 | A | 12/1999 | Waggoner et al. |
| 6,043,025 | A | 3/2000 | Minden et al. |
| 6,127,134 | A | 10/2000 | Minden et al. |
| 6,130,094 | A | 10/2000 | Waggoner et al. |
| 6,133,445 | A | 10/2000 | Waggoner et al. |
| 6,136,612 | A | 10/2000 | Della Ciana et al. |

(Continued)

FOREIGN PATENT DOCUMENTS

| EP | 1065250 | 1/2001 |
| EP | 1113822 | 7/2001 |

(Continued)

OTHER PUBLICATIONS

Achilefu et al. (2000) "Novel Receptor-Targeted Fluorescent Contract Agents for In Vivo Tumor Imaging," *Invest. Radiol.* 35:479-485.

(Continued)

*Primary Examiner* — Jacqueline Cheng
*Assistant Examiner* — Hien Nguyen
(74) *Attorney, Agent, or Firm* — Choate, Hall & Stewart, LLP

(57) ABSTRACT

The invention relates to systems and methods for tomographic imaging in diffuse media employing a fast reconstruction technique. A hybrid Fourier approach is presented that enables the fast tomographic reconstruction of large datasets. In certain embodiments, the invention features methods of in vivo fluorescence molecular tomographic (FMT) reconstruction of signals, reporters and/or agents (i.e., contrast agents or probes) in a diffusive medium (e.g., a mammalian subject). The method preserves the three-dimensional fluorophore distribution and quantitative nature of the FMT approach while substantially accelerating its computation speed, allowing FMT imaging of larger anatomies.

37 Claims, 8 Drawing Sheets

U.S. PATENT DOCUMENTS

| | | |
|---|---|---|
| 6,448,008 B1 | 9/2002 | Caputo et al. |
| 6,534,041 B1 | 3/2003 | Licha et al. |
| 6,615,063 B1 | 9/2003 | Ntziachristos et al. |
| 6,747,159 B2 | 6/2004 | Caputo et al. |
| 7,383,076 B2 | 6/2008 | Ntziachristos et al. |
| 7,445,767 B2 | 11/2008 | Licha et al. |
| 7,473,415 B2 | 1/2009 | Kawakami et al. |
| 7,488,468 B1 | 2/2009 | Miwa et al. |
| 7,547,721 B1 | 6/2009 | Miwa et al. |
| 7,647,091 B2 | 1/2010 | Ntziachristos et al. |
| 7,962,200 B2 | 6/2011 | Ntziachristos et al. |
| 2005/0283071 A1 | 12/2005 | Ripoll et al. |
| 2006/0184043 A1 | 8/2006 | Tromberg et al. |
| 2007/0238957 A1 | 10/2007 | Yared |
| 2008/0260647 A1 | 10/2008 | Intes et al. |
| 2008/0312879 A1 | 12/2008 | Fortier et al. |

FOREIGN PATENT DOCUMENTS

| | | |
|---|---|---|
| EP | 1480683 | 12/2004 |
| EP | 1679082 | 7/2006 |
| WO | WO-96/17628 | 6/1996 |
| WO | WO-97/40104 | 10/1997 |
| WO | WO-98/47538 | 10/1998 |
| WO | WO-99/51702 | 10/1999 |
| WO | WO-00/16810 | 3/2000 |
| WO | WO-01/21624 | 3/2001 |
| WO | WO-01/43781 | 6/2001 |
| WO | WO-03/074091 | 9/2003 |
| WO | WO-2006/072580 | 7/2006 |
| WO | WO-2009/055095 | 4/2009 |

OTHER PUBLICATIONS

Ai et al. (2007) "Exploration of New Chromophore Structures Leads to the Identification of Improved Blue Fluorescent Proteins," *Biochemistry* 46:5904-5910.
Aronson, R. (1995) "Boundary conditions for diffusion of light," *J. Opt. Soc. Am.* A 12:2532.
Baird et al. (2000) "Biochemistry, mutagenesis, and oligomerization of DsRed, a red fluorescent protein from coral," *Proc. Nat. Acad. Sci.* 97:11984-11989.
Ballou et al. (1997) "Tumor Detection and Visualization Using Cynanine Fluorochrome-Labeled Antibodies," *Biotechnol. Prog.* 13:649:658.
Becker et al. (2001) "Receptor-targeted optical imaging of tumors with near-infrared fluorescent ligands," *Nature Biotech.* 19:327-331.
Bremer et al. (2001) "In Vivo molecular target assessment of matrix metalloproteinase inhibition," *Nature Med.* 7:743-748.
Bugaj et al. (2001) "Novel fluorescent contrast agents for optical imaging of in vivo tumors based on a receptor-targeted dye-peptide conjugate platform," *J. Biomed. Opt.* 6:122-133.
Campbell et al. (2002) "A monomeric red fluorescent protein," *Proc. Nat. Acad. Sci.* 96:7877-7882.
Campo et al. (2007) "Polymeric Photosensitizer Prodrugs for Photodynamic Therapy," *Photochem. Photobiol.* 83:958-965.
Cubitt et al. (1995) "Understanding, improving and using green fluorescent proteins," *Trends Biochem Sci.* 11:448-455.
Giepmans et al. (2006) "The Fluorescent Toolbox for Assessing Protein Location and Function," *Science* 312:217-224.
Heikal et al. (2000) "Mollecular spectroscopy and dynamics of intrinsically fluorescent proteins: coral red (dsRed) and yellow (Citrine)," *Proc. Nat. Acad. Sci.* 97:11996-12001.
Heim et al. (1994) "Wavelength mutations and prostranslational autoxidation of green fluorescent protein," *Proc. Nat. Acad. Sci.* 91:12501-12504.
Heim et al. (1996) "Engineering green fluorescent protein for improved brightness, longer wavelengths and fluorescence resonance energy transfer," *Curr. Biol.* 6:178-182.

Lackowicz (1999) "Principals of Fluorescence Spectroscopy," 2nd Ed., Kluwar Academic, New York. pp. 87-88.
Li et al (1997) "Diffraction tomography for biochemical imaging with diffuse-photon density waves," *Optics Letters* 22:573-575.
Li et al (2000) "Near-field diffraction tomography with diffuse photon density waves," *Phys. Rev.* E 61 (4Pt B):4295-4309.
Markel et al (2001) "Inverse problem in optical diffusion tomography. I. Fournier-Laplace inversion formulas," *J. Opt Soc. Am. A. Opt. Image Sci. Vis.* 18(6):1336-1347.
Markel et al (2001) "Inverse scattering for the diffusion equation with general boundary conditions," *Phys. Rev. E* 64(3 Pt 2):035601.
Markel et al (2004) "Symmetries, inversion formulas, and image reconstruction for optical tomography," *Phys. Rev. E Stat. Nonlin. Soft Matter Phys.* 70(5 Pt 2):056616.
Matson et al (1997) "Three-dimensional tumor localization in thick tissue with the use of diffuse photon-density waves," *Applied Optics* 36:214-220.
Matson, C.L. (2002) "Diffraction Tomography for Turbid Media," *Advances in Imaging and Electron Physics* 124:253-342.
Neri et al. (1997)"Targeting by affinity-matured recombinant antibody fragments of an angiogenesis associated fibronectin isoform," *Nature Biotech.* 15:1271-1275.
Ozem et al (2000) "Infrared fluorescence sensing of submicromolar calcium: pushing the limits of photoinduced electron transfer," *Tetrahedron Letters* 9185-9188.
Rasmussen et al (2006) "Radiative transport in fluorescence-enhanced frequency domain photon migration," *Medical Physics* 4685-4700.
Ripoll et al (1999) "Scattering integral equations for diffusive waves: detection of objects buried in diffusive media in the presence of rough interfaces," *J. Opt. Soc. Am.* A16:1453.
Ripoll et al (1999) "Spatial resolution of diffuse photon density waves.", *J. Opt. Soc. Am.* A 16:1466-1476.
Ripoll et al (2001) "The Kirchhoff Approximation for diffusive waves.", *Phys. Rev.* E 64:051917.
Ripoll et al (2003) "Iterative boundary method for diffuse optical tomography.", *J. Opt. Soc. Am.* 20(6):1103-1110.
Ripoll et al (2005) "Experimental determination of photon propagation in highly absorbing and scattering media.", *J. Opt. Soc. Am.* A22(3):546-551.
Ripoll et al (2006) "From Finite to Infinite Volumes: Removal of Boundaries in Diffuse Wave Imaging," *Phys. Rev. Lett.* 96:173903.
Schotland et al (2001) "Inverse scattering with diffusing waves," *J. Opt. Soc. Am. A Opt. Image Sci. Vis.* 18(11):2767-2777.
Shaner et al. (2004) "Improved monomeric red, orange and yellow fluorescent proteins derived from *Discoma* sp red fluorescent protein," *Nat. Biotech* 22:1567-1572.
Shaner et al. (2005) "A Guide to Choosing Fluorescent Proteins," *Nature Methods* 2:905-909.
Tsien (1998) "The green fluorescent protein," *Ann. Rev. Biochem.* 67:509-544.
Tyagi et al. (1998) "Multicolor molecular beacons for allele discrimination," *Nat. Biotechnol.* 16:49-53.
Tyagi et al. (2000) "Wavelength-shifing molecular beacons," *Nat. Biotechnol.* 18:1191-1196.
Weissleder et al. (1999) "In vivo imaging of tumors with protease-activated hear-infrared fluorescent probes," *Nature Biotech.* 17:375-378.
Zhang et al. (2002) "Creating new fluorescent probes for cell biology," *Nat. Rev. Mol. Biol.* 3:906-918.
International Search Report of the International Searching Authority for PCT/US2010/046973 dated Apr. 29, 2011, 6 pages.
Written Opinion of the International Searching Authority for PCT/US2010/046973 dated Apr. 29, 2011, 11 pages.

FIGURE 3
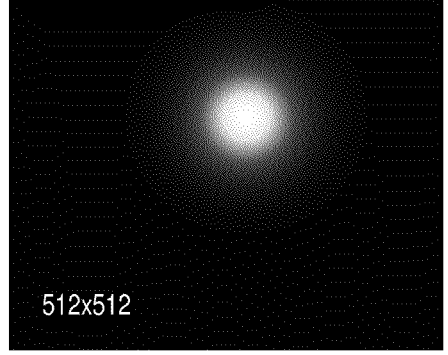
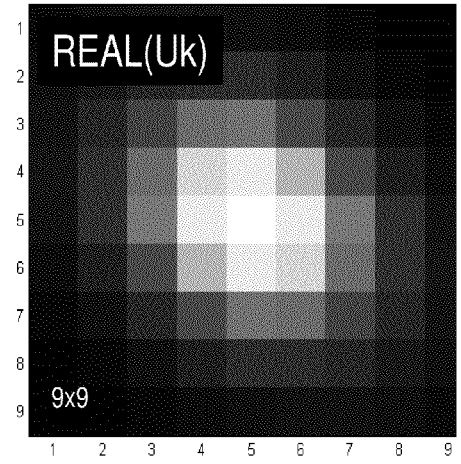
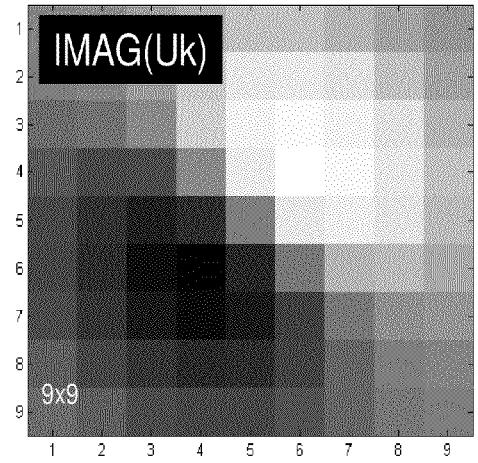

FIGURE 7
702
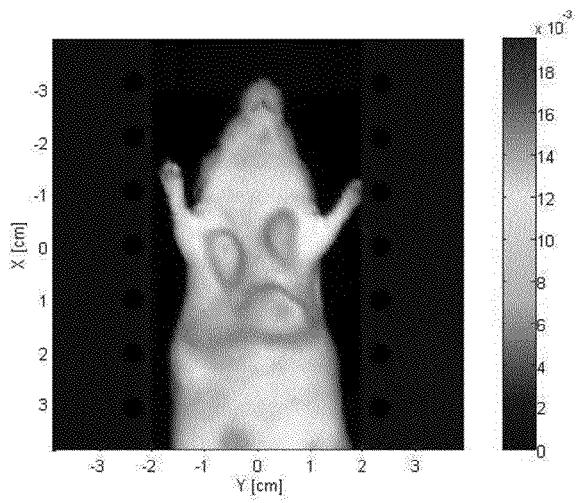
704
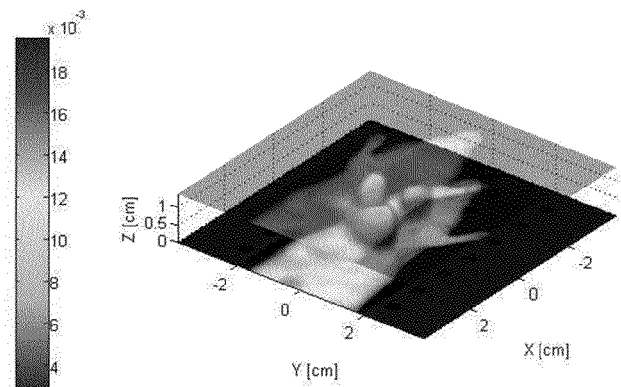

SYSTEMS AND METHODS FOR TOMOGRAPHIC IMAGING IN DIFFUSE MEDIA USING A HYBRID INVERSION TECHNIQUE

RELATED APPLICATION

This application claims priority to and the benefit of, and incorporates herein by reference in its entirety, U.S. Provisional Patent Application No. 61/238,075, which was filed on Aug. 28, 2009.

FIELD OF THE INVENTION

The invention relates generally to in vivo imaging systems and methods. More particularly, in certain embodiments, the invention relates to systems and methods for tomographic imaging employing a fast reconstruction technique.

BACKGROUND OF THE INVENTION

The amount of data used in optical tomography image reconstruction has increased by several orders of magnitude in recent years. This is primarily due to the use of large detector arrays, e.g., on the order of $10^3$ elements or higher. When coupled with a large number of sources, e.g., on the order of $10^2$ sources (such large number being facilitated, for example, by the use of non-contact measurements) large data sets easily in the range of $10^5$ source-detector pairs are generated. These large data sets reduce the ill-posed nature of the inversion, but also present an inherently large computational burden for reconstruction of tomographic images. Using traditional real-space weight matrix and Algebraic Reconstruction Techniques (ART) for the inversion yields impractically long computational times, in some instances longer that 24 hours. Similarly, using matrix-related inversion methods such as Singular Value Decomposition is not viable due to the amount of memory required. Thus, there is a need for a different approach that can handle large data sets and still maintain reasonably low computational times.

A powerful formalism for significantly reducing the number of measurements while maintaining the same amount of useful information is to work in Fourier Space. Diffuse light in the continuous wave (CW) regime is known to present only low spatial frequency contributions. By using all real-space data while selecting only a few low-frequency components in Fourier space, it is possible to benefit from the same amount of useful information while retaining a lower number of measurements.

Certain limited Fourier space techniques have been used to solve inverse problems in the past, for example, backprojection techniques and direct inversion techniques.

Backprojection suffers from being non-quantitative, low in resolution and incapable of good depth-discrimination [Matson, C. L., N. Clark, et al. (1997). "Three-dimensional tumor localization in thick tissue with the use of diffuse photon-density waves." Applied Optics 36: 214-220; Matson, C. L. (2002). "Diffraction Tomography for Turbid Media." Advances in Imaging and Electron Physics 124: 253-342; Li, X. D., T. Durduran, et al. (1997). "Diffraction tomography for biochemical imaging with diffuse-photon density waves." Optics Letters 22: 573-575; Li, X., D. N. Pattanayak, et al. (2000). "Near-field diffraction tomography with diffuse photon density waves." Phys Rev E 61(4 Pt B): 4295-309].

Complete Fourier approaches, also termed Direct Inversion, present severe reconstruction artifacts and generally are not applicable to datasets with fewer than $O(10^3)$ source positions [(Schotland, J. C. and V. A. Markel (2001). "Inverse scattering with diffusing waves." J Opt Soc Am A Opt Image Sci Vis 18(11): 2767-77; Markel, V. A. and J. C. Schotland (2001). "Inverse problem in optical diffusion tomography. I. Fourier-Laplace inversion formulas." J Opt Soc Am A Opt Image Sci Vis 18(6): 1336-47; Markel, V. A. and J. C. Schotland (2004). "Symmetries, inversion formulas, and image reconstruction for optical tomography." Phys Rev E Stat Nonlin Soft Matter Phys 70(5 Pt 2): 056616; Markel, V. A. and J. C. Schotland (2001). "Inverse scattering for the diffusion equation with general boundary conditions." Phys Rev E 64(3 Pt 2): 035601].

SUMMARY OF THE INVENTION

The invention presents a hybrid approach for fast reconstruction of tomographic images that offers advantages over backprojection and direct inversion techniques. In this hybrid approach, one or more subsets of large tomographic datasets are selected in frequency space (e.g., Fourier space) while one or more subsets are maintained in real space, then the weight matrix is inverted to obtain the tomographic representation of a region of interest within the subject in real space. This achieves fast computational times while maintaining good tomographic reconstruction performance.

For example, in preferred embodiments, the detector data is Fourier-transformed, while the sources and reconstructions are maintained in real-space. This enables the use of very large detector sets while still using lower numbers of sources (e.g., less than $10^2$) than the complete Fourier (direct inversion) approaches, and does not present the typical Fourier artifacts in the reconstruction because data is reconstructed in real space. This additionally enables full body imaging and the imaging of larger anatomies, since the total number of measurements in Fourier Space is very low but still represents the full body being imaged. Fast computation in larger scan fields is made possible, with both satisfactory spatial resolution and computation speed, allowing fluorescence molecular tomographic imaging of not only mice and rats, but also larger animals such as guinea pigs, rabbits, non-human primates, other mammals, and humans.

The invention provides systems and methods for transforming and selecting specific constituents of very large tomographic datasets for the purpose of reconstructing three-dimensional quantitative distributions of signal. These methods yield a faster yet still accurate depiction of the localization and distribution of the signal in the object/subject, including quantification and distribution of signals, reporters and/or agents (i.e., contrast agents or probes) in such objects/subjects than can be achieved by conventional tomographic reconstruction techniques.

In accordance with certain embodiments of the present invention, fast tomographic reconstruction methods and algorithms are described herein. The methods and algorithms have been fully parameterized to accommodate different imaging settings optimized for a variety of target objects/subjects and regions and a variety of different agents or probes. In particular, it is an object of the invention to provide such algorithms and corrected image analysis methods for use in biological research, as well as in preclinical and/or clinical settings. In particular, the present invention provides corrected imaging algorithms that can optionally be used with one or more imaging agent or probes for in vivo molecular imaging.

In one aspect, the invention provides a fluorescent molecular tomography system comprising: an excitation source; an optical imaging apparatus configured to direct light from the excitation light source into a subject at a plurality of locations; a detector configured to detect at multiple locations light emanating from a region of the subject; and a processor configured to process data corresponding to the detected light emanating from the region of the subject to produce a tomographic representation of the region of the subject, wherein the processor is configured to execute instructions to: (a) establish a forward model of excitation light propagation from the region to the detector using the data corresponding to the detected fluorescent light, wherein: (i) the excitation light source is represented in real space; (ii) the detected fluorescent light is represented in frequency space; and (iii) the forward model is established as a discretized weight matrix of normalized elements; and (b) invert the weight matrix to obtain the tomographic representation of the region of the subject in real space.

In certain embodiments, the detector is further configured to detect at multiple locations excitation light emanating from the subject, and wherein the processor is configured to execute instructions to establish the forward model using the data corresponding to the detected excitation light and the detected fluorescent light wherein the detected excitation light and the detected fluorescent light are represented in frequency space.

In certain embodiments, in the forward model, a surface of the subject is identified and boundary conditions are established for the surface. In addition, in the forward model, boundary removal equations can be used to convert data corresponding to the surface into a simulated infinite homogeneous medium, thereby simplifying the forward problem (see for example, Ripoll and Ntziachristos, "From Finite to Infinite Volumes: Removal of Boundaries in Diffuse Wave Imaging", Physical Review Letters 96, 173903, 2006). In certain embodiments, the data corresponding to the surface of the subject comprises an experimental measurement of surface flux distribution.

In certain embodiments, the detected fluorescent light is emitted from a probe within the region of the subject, and the forward model in (a) models excitation light propagation from the excitation light source to the probe and emitted fluorescent light propagation from the probe to the detector. In addition, in the forward model, a Born approximation is used to express an intensity of the detected fluorescent light emitted from the probe having spatially-varying concentration within the region. In certain embodiments, the intensity of the detected fluorescent light is normalized using an intensity of the spatially-corresponding detected excitation light. In addition, the forward model in (a) represents the detected excitation light and the detected fluorescent light in Fourier space.

In certain embodiments, the excitation light source or the optical imaging apparatus comprises a scanner configured to direct light into the subject at a plurality of locations, thereby defining a plurality of source locations. In certain embodiments, the plurality of source locations are non-uniformly spaced. In certain embodiments, the detector comprises an array of detector locations, and wherein the forward model is established using data obtained from the array of detector locations. In certain embodiments, there are substantially more detector locations than source locations.

In certain embodiments, the optical imaging apparatus comprises a chamber. In certain embodiments, the chamber is an animal chamber.

In certain embodiments, the subject is a human. In certain embodiments, the subject is a guinea pig, rabbit, non-human primate, or other mammal. In certain embodiments, the subject is a mouse, rat, amphibian, fish, or bird. The subject may be a vertebrate animal, for example, a mammal, including a human.

In certain embodiments, the excitation light is near-infrared light. In addition, the excitation light has a wavelength within a range from about 500 nanometers to about 1000 nanometers. In certain embodiments, the excitation light has a wavelength within a range from about 635 nanometers to about 850 nanometers.

In certain embodiments, the excitation light is continuous wave (CW) light. The excitation light comprises at least one member selected from the group consisting of continuous wave light, time-resolved light, and intensity modulated light.

In certain embodiments, the forward model models excitation light propagation from the excitation light source to the region of the subject and fluorescent light propagation from the region to the detector, where there is free space between the surface of the subject and the detector.

In another aspect, the present invention provides a method for imaging using the hybrid inversion technique to image the distribution of a fluorescent probe within a region of a subject, the method comprising the steps: (a) administering to the subject a probe comprising a visible or near-infrared fluorophore; (b) directing visible or near-infrared excitation light into the subject at multiple locations to transilluminate through or reflect from the region of the subject; (c) optionally detecting excitation light transmitted through or reflected from the region of the subject; (d) detecting fluorescent light emitted from the probe within the region of the subject; and (e) processing data corresponding to the detected fluorescent light, and, optionally, the detected excitation light, to provide a tomographic representation of the region of the subject, wherein the processing step comprises (i) establishing a forward model of excitation light propagation from an excitation light source to the probe within the region of the subject and of emission light propagation from the probe to a detector using the data corresponding to the detected fluorescent light and, optionally, the detected excitation light, wherein: (A) a surface of the subject is identified and boundary conditions are established for the surface, or, alternatively, boundary removal equations are used to convert data corresponding to the surface of the subject into a simulated infinite homogeneous medium, thereby simplifying the forward problem; (B) the excitation light source is represented in real space; (C) the detected fluorescent light and, optionally, the detected excitation light, is represented in frequency space; and (D) the forward model is established as a discretized weight matrix of normalized elements; and (ii) inverting the weight matrix to obtain the tomographic representation of the region of the subject in real space.

In certain embodiments, the step (c) comprises detecting excitation light transmitted through or reflected from the region of the subject, and wherein step (e) comprises processing data corresponding to the detected fluorescent light and the detected excitation light, wherein the processing step comprises establishing the forward model using the data corresponding to the detected fluorescent light and the detected excitation light, wherein the detected fluorescent light and the detected excitation light are represented in frequency space.

In another aspect, the present invention provides a method for imaging using a hybrid inversion technique to image the distribution of a fluorescence within a region of a subject, including but not limited to endogenous fluorescence, bioluminescence or fluorescent proteins, the method comprising: (a) directing excitation light into the subject at multiple locations to transilluminate through or reflect from at least a portion of the region of the subject containing the fluorescence; (b) optionally detecting excitation light transmitted through or reflected from the region of the subject; (c) detecting fluorescent light emitted from within the subject; and (d) processing data corresponding to the detected fluorescent light and the optionally detected excitation light to provide a tomographic representation of the region of the subject, wherein the processing step comprises (i) establishing a forward model of excitation light propagation from an excitation light source to the light source within the subject and of emission light propagation from the light source of the subject to a detector using the data corresponding to the optionally detected excitation light and the detected fluorescent light, wherein: (A) a surface of the subject is identified and boundary conditions are established for the surface, or, alternatively, boundary removal equations are used to convert data corresponding to the surface of the subject into a simulated infinite homogeneous medium, thereby simplifying the forward problem; (B) the excitation light source is represented in real space; (C) the detected fluorescent light and the optionally detected excitation light are represented in frequency space; and (D) the forward model is established as a discretized weight matrix of normalized elements; and (ii) inverting the weight matrix to obtain the tomographic representation of the region of the subject in real space.

In certain embodiments, the tomographic representation comprises a map of concentration of the probe within the region of the subject.

In addition, tomographic representation indicates an area of disease within a region of the subject. Furthermore, the tomographic representation can indicate an area of inflammation, arthritis, cancer, metastasis, plaque, infectious disease, cardiovascular disease, respiratory disease, metabolic disease, central nervous system disease, immune disease, neurodegenerative disease, dermatological disease, ophthalmic disease, cutaneous disease or a combination of two or more of the foregoing, within the region of the subject. In certain embodiments, the tomographic representation indicates a boundary of a disease site, such as a tumor within the region of the subject.

In certain embodiments, the probe used for imaging is an endogenous probe. In certain embodiments, the probe may be exogenous and administered to the subject.

In certain embodiments, the probe comprises a member selected from the group consisting of a molecular probe, a fluorescent molecular probe, a phototherapy based fluorescent probe, an activatable fluorescent probe, an enzyme-activatable fluorescent probe, an activity based probe, a targeted fluorescent probe, a near-infrared fluorescent molecular probe, a fluorescent protein, a fluorescent biomolecule, a non-specific fluorescent probe, quantum dots, a receptor-targeted near-infrared fluorochrome, an antibody- or antibody-like targeted near-infrared fluorochrome, a wavelength-shifting beacon, a multi-color fluorescence probe, and a lanthanide metal-ligand probe. In addition, the probe may comprise a fluorochrome attached to a delivery vehicle comprising any one or more of a polymer, a dendrimer, a protein, a carbohydrate, a lipid sphere, and a nanoparticle.

In certain embodiments, the method of imaging comprises administering to the subject a plurality of probes having optically distinguishable fluorescent emission wavelengths, detecting fluorescent light emitted from each of the probes, and processing data corresponding to the detected light to provide one or more tomographic representations. In addition, the effect of the probe on the region within the object may be determined using the tomographic representation. Furthermore, the method may comprise imaging at excitation and emission wavelengths of a natural tissue chromophore.

In certain embodiments, imaging steps (b), (c), (d), and (e) may be repeated to obtain tomographic representations as a function of time. In addition, the kinetics of a distribution of the probe within the region can be monitored using tomographic representations. The kinetics of activation of the probe can be monitored using tomographic representations.

In certain embodiments, the method may comprise imaging at excitation and emission wavelengths of a natural tissue chromophore.

In certain embodiments, the tomographic representation comprises a map showing quantity of the probe in three dimensions. The tomographic representation may comprise one or more images, and wherein the method further comprises storing the one or more images, displaying the one or more images, or both storing and displaying the one or more images. In addition, the tomographic representation comprises a three-dimensional tomographic image and the method further comprises the step of combining the three-dimensional tomographic image with photographic, pictorial, magnetic resonance, x-ray computed tomography, ultrasound, single photon emission tomography, or positron-emission tomography imaging data and representations.

In certain embodiments, the imaging method further comprises the step of detecting or monitoring a cellular abnormality or disease using tomographic representation. The cellular abnormality or disease can comprise at least one member selected from the group consisting of cancer, oncological disease, infectious disease, metabolic disease, respiratory disease, cardiovascular disease, AIDS, immune disease, central nervous system disease, neurodegenerative disease, inflammation, dermatological disease, ophthalmic disease, cutaneous disease, inherited diseases, environmental diseases, bone-related diseases, immunologic disease, and surgery-related complications.

In certain embodiments, the subject of the imaging method is a mammal. In certain embodiments, the subject is a human. In certain embodiments, the subject is a guinea pig, rabbit, non-human primate, or other mammal. In certain embodiments, the subject is a mouse, rat, amphibian, fish, or bird. The subject may be a vertebrate animal, for example, a mammal, including a human.

In certain embodiments, the probe of the imaging method may comprise an endogenous fluorophore that is encoded by a gene within the subject. The expression of the gene encoding the fluorophore can be determined using tomographic representation. The endogenous fluorophore can be a fluorescent protein or biomolecule, including but not limited to green, red and infrared fluorescent proteins.

In another aspect, the invention is an apparatus for reconstructing a tomographic representation of a probe within a region of the subject, the apparatus comprising: a memory that stores code defining a set of instructions; and a processor that executes the instructions thereby to: (a) establish a forward model of excitation light propagation from an excitation light source to the probe within the region of the subject and of emission light propagation from the probe to a detector using data corresponding to detected fluorescent light, wherein: (i) a surface of the subject is identified and step (A) and/or step (B) is/are performed: (A) boundary conditions are established for the surface, and (B) boundary removal equations are used to convert data corresponding to the surface of the subject into a simulated infinite homogenous medium, thereby simplifying the forward problem; (ii) the excitation light source is represented in real space; (iii) the detected fluorescent light is represented in frequency space; and (iv) the forward model is established is as a discretized weight matrix of normalized elements; and (b) invert the weight matrix to obtain the tomographic representation of the region of the subject in real space.

In certain embodiments, the processor executes the instructions to establish the forward model using data corresponding to detected excitation light and the detected fluorescent light, wherein the detected fluorescent light and the detected excitation light are represented in frequency space.

In another aspect, the invention provides a diffuse optical tomography system comprising one or more illumination sources; an optical imaging apparatus configured to direct light from the at least one illumination source into a subject at a plurality of locations; a detector configured to detect at multiple locations light emanating from the subject to obtain a first and second measurement, wherein the first measurement is a reference measurement and the second measurement corresponds to absorption of at least a portion of the illuminating light as it passes through a light-absorbing region within the subject, and wherein the reference measurement does not reflect all of said absorption; and a processor configured to process data corresponding to the first and second measurements of detected light emanating from the subject, wherein the processor is configured to execute instructions to: (a) establish a forward model of light propagation from at least one of the one or more illumination sources to the light-absorbing region within the subject and of light propagation from the region to the detector using the data corresponding to the first and second measurements, wherein: (i) the at least one illumination source is represented in real space; (ii) the detected light is represented in frequency space; and (iii) the forward model is established as a discretized weight matrix of normalized elements; and (b) invert the weight matrix to obtain the tomographic representation of the region of the subject in real space. In addition, the system can comprise at least two illumination sources emitting light having different wavelengths. In certain embodiments, the at least two illumination sources are near-infrared light sources.

In certain embodiments, a diffuse optical tomography imaging system can comprise at least two illumination sources with different wavelengths comprising a wavelength below an isosbestic point of an oxy-hemoglobin (HbO) and a deoxy-hemoglobin (Hb), and a wavelength above the isosbestic point.

Elements of embodiments described with respect to a given aspect of the invention may be used in various embodiments of another aspect of the invention Other features and advantages of the invention will be apparent from the following figures, detailed description, and the claims.

The objects and features of the invention can be better understood with reference to the drawings described below, and the claims. In the drawings, like numerals are used to indicate like parts throughout the various views.

BRIEF DESCRIPTION OF DRAWINGS

FIG. 3 are images comparatively depicting the real-space intensity of a point source and the absolute value of its Fourier transform, according to an illustrative embodiment of the invention.

FIG. 7 is a schematic showing a volume rendering of an in vivo dataset from a tumor-bearing mouse injected with a fluorescent contrast agent, according to an illustrative embodiment of the invention.

DETAILED DESCRIPTION

Figure 1:
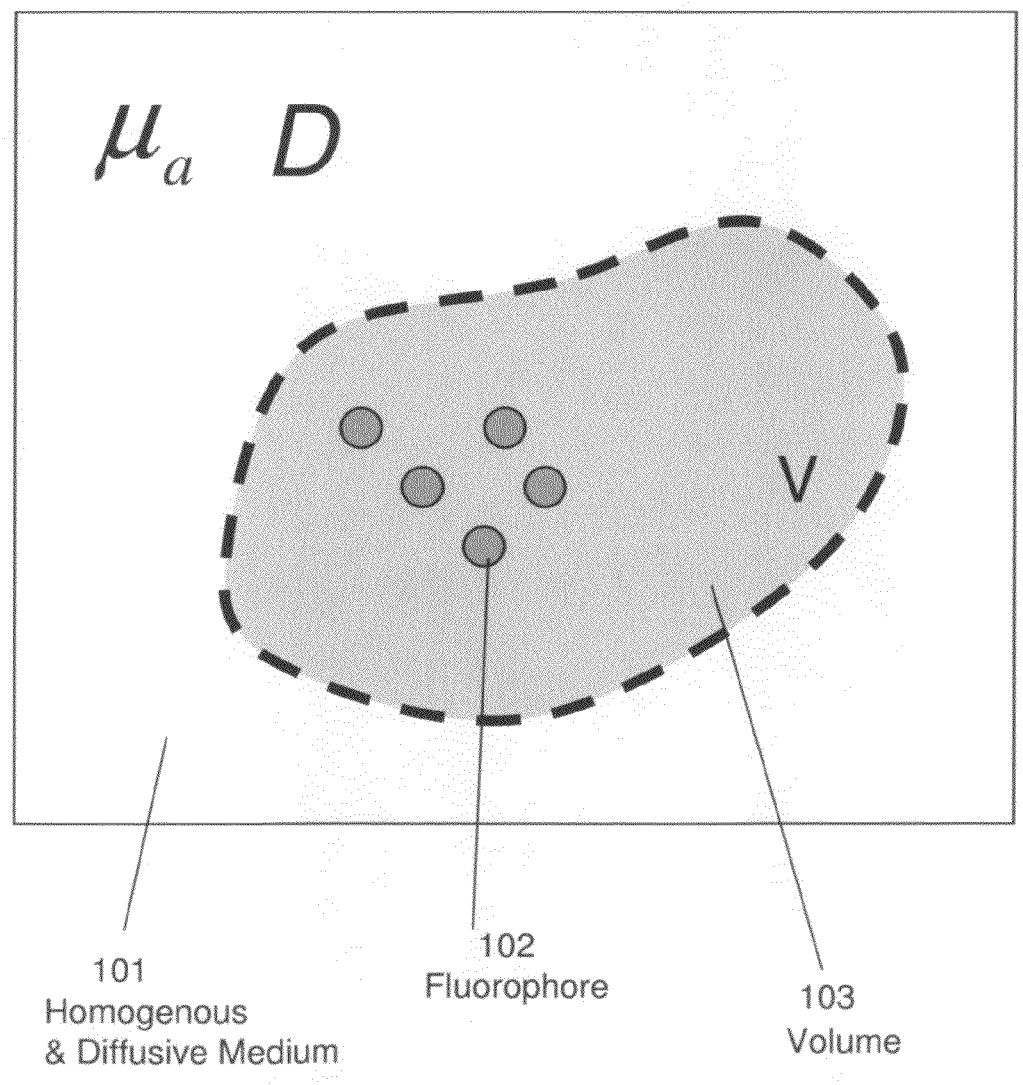
FIG. 1 is a schematic drawing depicting a collection of fluorophores within a volume V in an otherwise infinite homogeneous and diffusive medium, in accordance with an illustrative embodiment of the invention.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

As used herein, the term "image" is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout).

The term "tomographic image" may refer, for example, to an optical tomographic image, an x-ray tomographic image, a tomographic image generated by magnetic resonance, positron emission tomography (PET), magnetic resonance, (MR) single photon emission computed tomography (SPECT), and/or ultrasound, and any combination of these.

The term "excitation image" is understood to mean an image acquired at the wavelength corresponding to that of the exposing light source, of said exposing light emanating from the object being imaged.

The terms "fluorescence image" or "emission image" are understood to mean an image acquired at the wavelength corresponding to the emission wavelength of a fluorescent agent or probe.

The term "residual image" is understood to mean the image resulting from the mathematical operation of subtracting a corrective term, for example an image, from an original image, for example a fluorescence image.

As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume, and the three-dimensional map may be displayed in two-dimensions.

As used herein, the term "electromagnetic radiation" is understood to mean self-propagating waves in space of electric and magnetic components that oscillate at right angles to each other and to the direction of propagation, and are in phase with each other. Electromagnetic radiation includes: radio waves, microwaves, red, infrared, and near-infrared light, visible light, ultraviolet light, X-rays and gamma rays.

As used herein the term "image acquisition device" includes any detector of electromagnetic radiation including, but not limited to, CCD camera, photomultiplier tubes, photodiodes, and avalanche photodiodes.

As used herein, the term "real space" is understood to mean the domain defined by spatial coordinates.

As used herein, the term "frequency space" is understood to mean the domain defined by the frequency of spatial variation of intensity.

As used herein the term "hybrid method" or "hybrid approach" refers to a methodology that uses a combination of real-space expressions with Fourier-domain data and expressions.

As used herein, the term "forward model" is understood to mean a physical model of light propagation in a given medium from a source to a detector.

A technique is described herein for tomographic reconstruction that combines real-space representation of data, real-space transformation, and Fourier transformation on subsets of tomographic datasets as described herein to perform fast tomographic reconstruction prior to image display and/or analysis. For the purposes of illustration, an illustrative, non-limiting description is provided for a method of fluorescence tomographic reconstruction in vivo of objects, e.g., reporters and/or agents such as contrast agents or probes, in a diffusive medium (e.g., a mammalian subject). This technique can be used in any of the tomographic systems described herein.

Fluorescence Molecular Tomography, abbreviated as FMT (sometimes also referred to as Fluorescence Mediated Tomography) or Diffuse Optical Tomography (when used to image concentration of absorbers), abbreviated as DOT, provide a method of in vivo imaging including the steps of administering to a subject an optical imaging probe; directing excitation light into the subject at multiple locations; optionally detecting excitation light emanating from the subject; detecting optical light emitted from one or more probes within the subject; and processing data corresponding to the detected fluorescent light emitted from the probe within the subject and, optionally, the detected excitation light emanating from the subject, to provide a tomographic representation of the region within the subject. The processing of data corresponding to both the detected excitation light and detected fluorescent light comprises simulating photon propagation at the excitation wavelength and simulating photon propagation at the emission wavelength to obtain a prediction of one or more quantitative measurements of the probe, such as concentration or total accumulation in a region within the object, and can also include additional steps of applying statistical optimal estimation and coincidence masking techniques to predict and compensate for waveguiding effects (see for example International Patent Application No. PCT/US2008/65648 "Imaging Systems Featuring Waveguiding Compensation," the text of which is incorporated by reference herein, in its entirety). The steps can also be repeated at predetermined intervals, thereby allowing for the evaluation of the subject over time. The subject may be a vertebrate animal, for example, a mammal, including a human. The subject may also be a non-vertebrate (for example, *C. elegans, drosophila*, or another model research organism, etc.) used in laboratory research.

In certain embodiments, the present invention can be used in FMT as well as DOT imaging systems. DOT is a technique that offers the capability to quantify changes in absorption present in highly scattering media such as tissue. Its theoretical principles are similar to FMT in the sense that sources need to be scanned on the object and light detected at a detector, assuming that light diffuses within the volume. In order for an absorption perturbation to be imaged in this modality a reference image where light has not been absorbed or that has been absorbed in a lesser manner needs to be taken. After this measurement, equivalent to the excitation measurement in FMT, a measurement where this absorption is present is acquired (equivalent to the emission measurement in FMT). By choosing appropriate wavelengths (e.g., in the near infrared), this technique may simultaneously quantify the tissue concentration of both oxy-(HbO) and deoxy-hemoglobin (Hb), and thus the oxygen saturation and blood volume. Typically, two or more near-infrared sources, chosen on both sides of the isosbestic point of the oxy/deoxyhemoglobin absorption spectrum (near 800 nm) are used to illuminate the tissue at various locations. The light intensity distribution at the tissue surface thus contains both spectral and spatial information about subsurface absorbers.

In certain embodiments, the invention can be used within a FMT imaging system comprising: an excitation light source; an optical imaging apparatus configured to direct light from the excitation light source into a subject at a plurality of locations; a detector configured to detect at multiple locations excitation light emanating from the subject and fluorescent light emanating from a region within the subject; and a processor configured to process data corresponding to the detected excitation light emanating from the subject and data corresponding to the detected fluorescent light emanating from the region of the subject to produce a tomographic representation of the region of the subject. The processor is configured to execute instructions to establish a forward model of excitation light propagation from the excitation light source to the region of the subject and of fluorescent light propagation from the region to the detector using the data corresponding to the detected excitation light and the detected fluorescent light. The excitation light source is represented in real space while the detected excitation light and the detected fluorescent light are represented in frequency space. Finally, the forward model is established as a discretized weight matrix of normalized elements; and the weight matrix is inverted to obtain the tomographic representation of the region of the subject in real space.

In the forward model, a surface of the subject is identified and boundary conditions are established for the surface. Furthermore, boundary removal equations are used to convert data corresponding to the surface of the subject into a simulated infinite homogeneous medium, thereby simplifying the forward model. The data corresponding to the surface of the subject comprises an experimental measurement of surface flux distribution. The forward model then models excitation light propagation from the excitation light source to the region of the subject and fluorescent light propagation from the region to the detector, where there is free space between the surface of the subject and the detector.

In certain embodiments, the detected fluorescent light is emitted from a probe within the region of the subject, and the forward model then models excitation light propagation from the excitation light source to the probe and emitted fluorescent light propagation from the probe to the detector. In the forward model, a Born approximation is used to express an intensity of the detected fluorescent light emitted from the probe having spatially-varying concentration within the region. The intensity of the detected fluorescent light is normalized using an intensity of the spatially-corresponding detected excitation light.

In other embodiments, the forward model represents the detected excitation light and the detected fluorescent light in Fourier space. In the system, the excitation light source or the optical imaging apparatus comprises a scanner configured to direct light into the subject at a plurality of locations, thereby defining a plurality of source locations. With hybrid inversion, a non-uniform grid of any number of sources can be used. The detector comprises an array of detector locations and the forward model is established using data obtained from a plurality of detector locations.

In certain embodiments of the system, the excitation light is near-infrared. The excitation light has wavelength within a range from about 500 nanometers to about 1000 nanometers. In other embodiments of the system, the excitation light has wavelength within a range from about 635 nanometers to about 850 nanometers. Furthermore, the excitation light is continuous wave (CW) light. The excitation light comprises at least one member selected from the group consisting of continuous wave light, time-resolved light, and intensity modulated light.

The method and algorithm accept as input raw scan images generated by a fluorescence molecular tomography (FMT) system acquisition of any object. As described in U.S. Pat. No. 6,615,063, and U.S. Pat. No. 7,383,076, each entitled, "Fluorescence-Mediated Molecular Tomography"; U.S. patent application Ser. No. 11/003,936 "Imaging Volumes with Arbitrary Geometries in Contact and Non-Contact Tomography", published as US 2005/0283071 on Dec. 22, 2005; and U.S. Pat. No. 7,647,091, "Method and System for Free Space Optical Tomography of Diffuse Media", the texts of which are incorporated herein by reference in their entirety, FMT-generated raw scan images contain images at both the excitation wavelength of the light source, called "excitation images", and at the emission wavelength of the contrast agent, interchangeably called "emission images" or "fluorescence images", for a multiplicity of source and/or detector locations.

The detected light preferably includes excitation light from the light source that has been transmitted through or reflected from the object and fluorescent light emitted from one or more fluorophore within the object. In the case of DOT, only the excitation light from the light source that has been transmitted through the object is detected. Data corresponding to the excitation light transmitted through or reflected from the object can be used to correct/calibrate captured fluorescent measurements, thereby providing more accurate tomographic images. The one or more fluorophore emits fluorescent light as a result of excitation by the excitation light. Background fluorescence may be accounted for by obtaining background measurements and processing data corresponding to the captured fluorescent light accordingly. For example, the method may include the step of detecting a background signal, where the processing step includes generating a corrected measurement of the detected fluorescent light and/or a corrected measurement of the detected excitation light using data corresponding to the detected background signal, and using the corrected measurement(s) in the optical tomographic reconstruction. In certain embodiments, the processing step includes generating a corrected measurement of the detected fluorescent light and a corrected measurement of the detected excitation light using data corresponding to the detected background light, generating a calibrated fluorescent measurement from the corrected fluorescent measurement and the corrected excitation light measurement, and using the calibrated fluorescent measurement in the optical tomographic reconstruction.

Data corresponding to the detected light may be used as input in the optical tomographic and/or planar reconstruction, for example, in an iterative process. In certain embodiments, the steps of the method are repeated to obtain a plurality of tomographic and/or planar images. In certain embodiments, the steps of the method are repeated to obtain tomographic representations as a function of time. In other embodiments, the kinetics of distribution of a probe within a region are monitored using tomographic representations. In another aspect, the kinetics of activation of a probe within a region are monitored using tomographic representations.

In other embodiments, the invention is a method of imaging a distribution of a fluorescent probe within a region of a subject, the method comprising: (a) administering to the subject a probe comprising a visible or near-infrared fluorophore; (b) directing visible or near-infrared excitation light into the subject at multiple locations to reflect from or transilluminate at least a portion of the region of the subject containing the fluorescent probe; (c) optionally detecting excitation light transmitted through or reflected from the region of the subject; (d) detecting fluorescent light emitted from the probe within the subject; and (e) processing data corresponding to the detected fluorescent light and the optionally detected excitation light to provide a tomographic representation of the region of the subject, wherein the processing step comprises: (i) establishing a forward model of excitation light propagation from an excitation light source to the probe within the subject and of emission light propagation from the probe to a detector using the data corresponding to the optionally detected excitation light and the detected fluorescent light, wherein: (A) a surface of the subject is identified and boundary conditions are established for the surface, or, alternatively, boundary removal equations are used to convert data corresponding to the surface of the subject into a simulated infinite homogeneous medium, thereby simplifying the forward problem; (B) the excitation light source is represented in real space; (C) the detected fluorescent light and the optionally detected excitation light are represented in frequency space; and (D) the forward model is established as a discretized weight matrix of normalized elements; and (ii) inverting the weight matrix to obtain the tomographic representation of the region of the subject in real space.

In certain embodiments, the tomographic representation comprises a map of concentration of the probe within the region of the subject. In other embodiments, the tomographic representation comprises a map showing quantity of the probe in three dimensions. In addition, the tomographic representation comprises one or more images, and wherein the method further comprises storing the one or more images, displaying the one or more images, or both storing and displaying the one or more images. In other embodiments, the tomographic representation comprises a three-dimensional tomographic image and wherein the method further comprises the step of combining the three-dimensional tomographic image with magnetic resonance, x-ray computed tomography, ultrasound, single photon emission tomography, or positron emission tomography imaging data.

In certain embodiments, the probe used for imaging is an endogenous probe. Furthermore, the probe may comprise an endogenous fluorophore that is encoded by a gene within the subject. In other embodiments, the invention is a method for determining expression of the gene encoding the fluorophore using the tomographic representation. In other embodiments, the endogenous fluorophore is a fluorescent protein or biomolecule. In other embodiments, the invention is a method comprising the step of imaging at excitation and emission wavelengths of a natural tissue chromophore.

In other embodiments, the probe used for imaging is administered to the subject. In certain embodiments, the invention includes methods for imaging with probes wherein step (a) comprises administering to the subject a plurality of probes having optically distinguishable fluorescent emission wavelengths, step (d) comprises detecting fluorescent light emitted from each of the probes, and step (e) comprises processing data corresponding to the detected light to provide one or more tomographic representations. In other embodiments, the invention is used to determine an effect of the probe on the region within the object using the tomographic representation. The probe comprises a member selected from the group consisting of a molecular probe, a fluorescent molecular probe, an activatable fluorescent probe, an enzyme-activatable fluorescent probe, a targeted fluorescent probe, a near-infrared fluorescent molecular probe, a fluorescent protein, a fluorescent biomolecule, a non-specific fluorescent probe, quantum dots, a receptor-targeted near-infrared fluorochrome, an antibody-targeted near-infrared fluorochrome, a wavelength-shifting beacon, a multi-color fluorescence probe, and a lanthanide metal-ligand probe. In other embodiments, the probe comprises a fluorochrome attached to a delivery vehicle comprising any one or more of a polymer, a dendrimer, a protein, a carbohydrate, a lipid sphere, and a nanoparticle.

In another aspect, the invention relates to a method of imaging a target volume of an object, the method including the steps of directing excitation radiation into the object at multiple locations; optionally detecting excitation radiation transmitted through or reflected from the object; detecting radiation at a surface of the object; detecting radiation emitted from one or more contrast agents/probes within the object; and processing data corresponding to the detected radiation transmitted through or reflected from the object, the optionally detected excitation radiation transmitted through or reflected from the object, and the detected radiation emitted from the one or more contrast agents/probes within the object to provide one or more images of the target volume of the object. The method may further include the step of displaying the image. The object may be, for example, an animal, for example, a mammal, or a human.

In another aspect, the invention relates to a method for detecting disease. In certain embodiments, the tomographic representation indicates an area of disease within the region of the subject. In other embodiments, the tomographic representation indicates an area of arthritis, cancer, metastasis, plaque, or a combination of two or more of the foregoing, within the region of the subject. In other embodiments, the tomographic representation indicates a boundary of a tumor within the region of the subject. In other embodiments, the tomographic representation can be used to detect or monitor a cellular abnormality or disease. Furthermore, the cellular abnormality or disease comprises at least one member selected from the group consisting of cardiovascular disease, AIDS, neurodegenerative disease, inflammation, dermatological disease, ophthalmic disease, cutaneous disease, and immunologic disease.

Algorithms that support preferred embodiments of the invention are detailed below. FIG. 1 is a schematic drawing depicting a collection of fluorophores 102 within a volume V 103 in an otherwise infinite homogeneous and diffusive medium 101. The geometry shown in FIG. 1, consists of a diffusive volume V 103 bounded by surface S, which separates it from an outer non-diffusive medium of refractive index $n_{out}$ (however, presented further below are Boundary Removal equations, which are used herein to convert the 3D surface data into an infinite homogenous medium, where, effectively, volume V becomes infinite, filling all space with a diffusive medium of constant properties D, $\mu_a$, and $n_{in}$). The diffusive medium is characterized by its absorption coefficient $\mu_a$, its reduced scattering coefficient $\mu_s'$ (defined as $\mu_s' = \mu_s(1-g)$, where g is the anisotropy factor), and its average refractive index $n_{in}$. In a highly absorbing and scattering medium the diffusion coefficient may be defined as $D = \frac{1}{3}(\mu_s' + \alpha\mu_a)$, the factor $\alpha$ depending non-linearly on the optical properties and having typically values between $\alpha = 0.2$ to $\alpha = 0.6$ (see Ripoll, J., D. Yessayan, et al. (2004). "Experimental determination of photon propagation in highly absorbing and scattering media." J. Opt. Soc. Am. A 22(3) and references therein for a deeper study of this factor and experimental validation). Typical values of $\alpha$ for tissue in the visible (where tissue absorption is greater) are in the order of $\alpha = 0.5$ for typical values of anisotropy in tissue of $g \sim 0.8$. In preferred embodiments, the invention deals directly with D and $\mu_a$, instead of $\mu_s'$ and $\mu_a$, assuming they are related through the above mentioned expression. Additionally, all derivation is done in the frequency domain, with the extrapolation to time-domain through a Fourier transform, or to the CW regime by selecting the zero frequency being straightforward.

For illustrative purposes, assume that in the volume V 103 of FIG. 1, a point source located at $r_s$ inside the medium whose intensity is modulated at a frequency $\omega$. In this case, the average intensity U may be expressed as $U(r,t) = U(r)\exp[-i\omega t]$. Accounting for energy conservation in the Radiative Transfer Equation, the U detected at r within V represents a diffuse photon density wave (DPDW) and obeys the Helmholtz equation:

$$\nabla^2 U(r) + \kappa_0^2 U(r) = -\frac{S(r)}{D} \quad r \in V, \qquad (1)$$

with a complex wave-number $\kappa_0$ given by:

$$\kappa_0 = \left(-\frac{\mu_a}{D} + i\frac{\omega n_{in}}{cD}\right)^{1/2} \qquad (2)$$

where c is the speed of light in vacuum and S(r) is the source distribution. In an infinite homogeneous 3D medium the Green function is given by:

$$g(\kappa_0|r_s - r_d|) = \frac{\exp(i\kappa_0|r_s - r_d|)}{D|r_s - r_d|} \quad (3)$$

Taking into account the boundary S, the average intensity U inside volume V is found through Green's theorem as [J. Ripoll and M. Nieto-Vesperinas, J. Opt. Soc. Am. A 16, 1453 (1999)]:

$$U(r_d) = \quad (4)$$
$$U^{(inc)}(r_d) - \frac{1}{4\pi} \int_S \left[ U(r') \frac{\partial g(\kappa|r' - r_d|)}{\partial \hat{n}'} - g(\kappa|r' - r_d|) \frac{\partial U(r')}{\partial \hat{n}'} \right] dS',$$

where $$U^{(inc)}(r) = \int_V S(r) g(\kappa_0|r_s - r_d|) d^3 r \quad (5)$$

is the average intensity that is obtained in the absence of the surface. One can use Fick's Law:

$$J_n(r) = J(r) \cdot \hat{n} = -D \frac{\partial U(r)}{\partial \hat{n}} \quad (6)$$

and the boundary condition between the diffusive and non-diffusive medium (R. Aronson, J. Opt. Soc. Am. A 12, 2532 (1995)):

$$U(r)|_S = -C_{nd} D \frac{\partial U(r)}{\partial \hat{n}}\Big|_S, \, r \in S \quad (7)$$

where the coefficient $C_{nd}$ takes into account the refractive index mismatch between both media (R. Aronson, J. Opt. Soc. Am. A 12, 2532 (1995)). In the case of index matched media, i.e. $n_{out}=n_{in}$, $C_{nd}=2$, whereas for typical tissue/air index values (nin=1.333, nout=1) $C_{nd}\sim 5$. Making use of Eqs. (6) and (7) in Eq. (4), there is a convenient expression which depends solely on the total flux $J_n$ so that Eq. (4) can be rewritten as:

$$U(r) = \quad (8)$$
$$U^{(inc)}(r) + \frac{1}{4\pi D} \int_S \left[ C_{nd} D \frac{\partial g(\kappa|r' - r|)}{\partial n'} + g(\kappa|r' - r|) \right] J_n(r') dS',$$
$$r \in V$$

Eq. (8) forms the basis of the Boundary Removal equations, that can be used to convert the 3D surface data into an infinite homogenous medium. In solving the integral Eq. (8), the surface flux $J_n$ or the average intensity U can be solved for at the boundary. This can be achieved by using accurate algorithms such as the Diffuse Reflectance Boundary Method (Ripoll, J. and V. Ntziachristos (2003). "Iterative boundary method for diffuse optical tomography." J. Opt. Soc. Am. A 20(6): 1103-1110.) or approximations to it such as the Kirchhoff Approximation (Ripoll, J., V. Ntziachristos, et al. (2001). "The Kirchhoff Approximation for diffusive waves." Phys. Rev. E 64: 051917: 1-8.). Note that the Green functions, g, involved in Eq. (8) are infinite Green's functions.

In an experimental setup which enables the detection of light that emerges from all points of the surface S, it is possible to experimentally measure the distribution of emerging flux Jn. In this case Jn does not need to be calculated from Eqs. (6) and (7) but can be directly substituted by the experimental measurement. Such measurements are possible using a non-contact approach by projecting onto the surface the values measured at a CCD detector. A non-contact setup can capture with great accuracy and spatial sampling the distribution of total outward flux on the boundary. In the case that Jn is known, it is possible to obtain from Eq. (8) $U^{(inc)}$, i.e. the average intensity created by the source distribution in the absence of the interface. This means that volume V has become effectively infinite, filling all space with a diffusive medium of constant properties D, $\mu_a$ and $n_{in}$. The measured infinite-case average intensity at each detector position r can be found as:

$$U^{(inc)}(r) = \quad (9)$$
$$C_{nd} J_n(r) - \frac{1}{4\pi D} \int_S \left[ C_{nd} D \frac{\partial g(\kappa_0|r - r'|)}{\partial n'} + g(\kappa_0|r - r'|) \right] J_n(r') dS',$$
$$r \in S$$
$$\forall r' \neq r$$

Once the data obtained from a generic 3D surface has been transformed into "Infinite Homogeneous" data, this illustrative method proceeds with an inversion approach that uses solely infinite homogeneous Green functions. The following description uses the expression for g shown in Eq. (3).

It is assumed that within volume V 106 there is a collection of fluorophores 104 with spatially-dependant concentration F(r). The Fluorescence intensity due to a collection of fluorophores with Concentration F(r) distributed within a volume V in an otherwise infinite space may be expressed within the Born approximation as:

$$U_{fl}(r_s, r_d) = \int_V U^{(inc)}(r_s, r) F(r) g(r, r_d) dr \quad (10)$$

Figure 2:
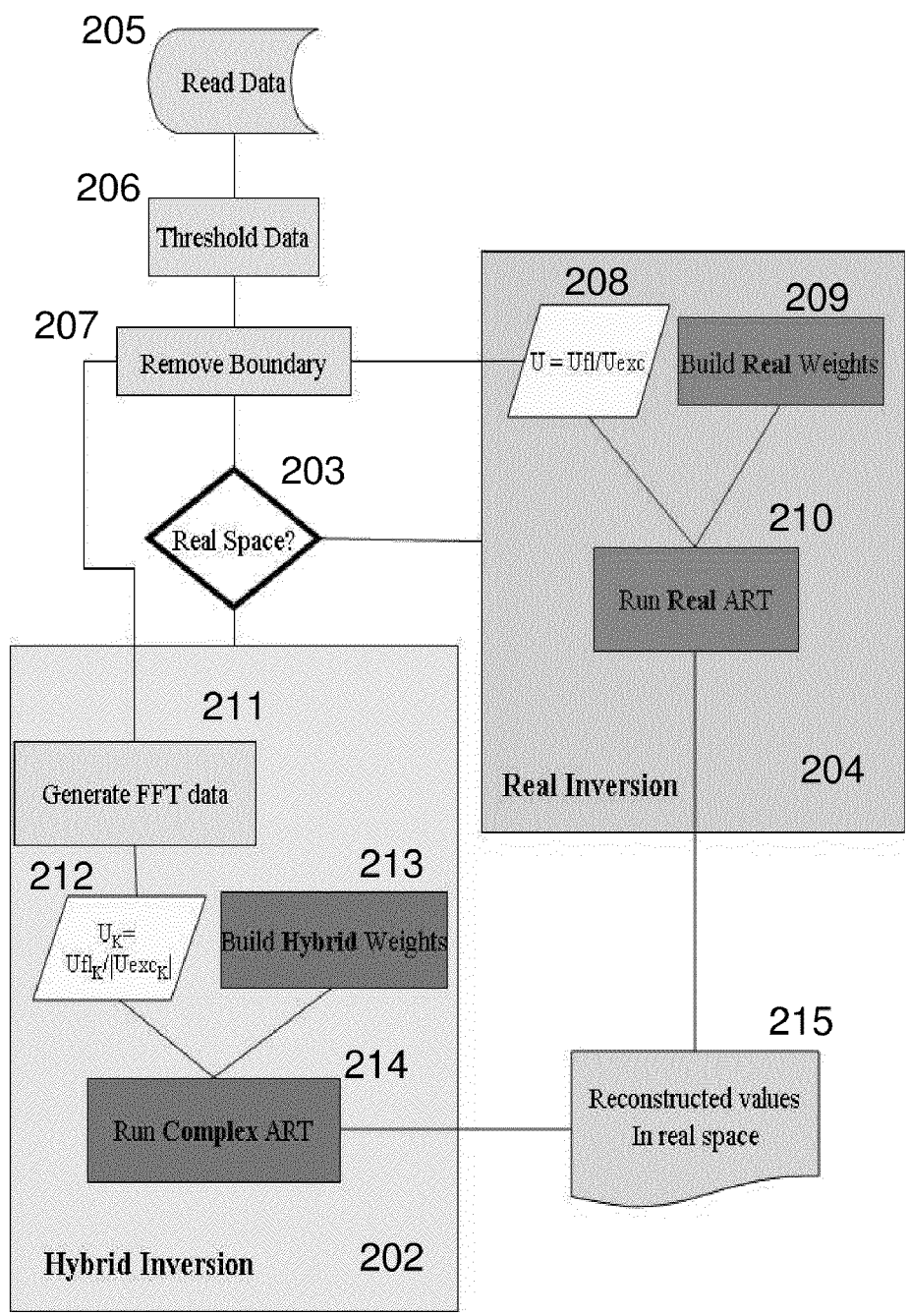
FIG. 2 is a block diagram of the steps of a method for obtaining a 3D map of an unknown fluorescing or absorbing probe, tissue, or other target object in a subject, according to an illustrative embodiment of the invention.

Assume a detector plane at $z_d$, as shown in FIG. 2. Rewriting $r_d$ and r as $r_d=(R_d, z_d)$ and r=(R,z) respectively, $$U_{fl}(R_s, R_d; z_s, z_d) = \int_V U^{(inc)}(r_s, r) F(r) g(R, R_d; z, z_d) dr \quad (11)$$

A Fourier transform can be performed on the detector plane $z_d$:

$$\tilde{U}_{fl}(R_s, K_d; z_s, z_d) = \int_V U^{(inc)}(r_s, r) F(r) \tilde{g}(R, K_d; z, z_d) dr \quad (12)$$

where:

$$\tilde{g}(R, K_d; z, z_d) = \int_{-\infty}^{+\infty} \frac{\exp(i\kappa_0|r - r_d|)}{|r - r_d|} \exp(i K_d R_d) dR_d \quad (13)$$

is the Fourier Transform on the detectors of the infinite Green's function which can be written as (Ripoll, J., M. Nieto-Vesperinas, et al. (1999). "Spatial resolution of diffuse photon density waves." J. Opt. Soc. Am. A 16: 1466-1476):

$$\tilde{g}(R, K_d; z, z_d) = \frac{2\pi i}{q(K_d)} \exp(iq(K_d)(z_d - z)) \exp(i K_d R) \quad (14)$$

assuming that in transmission mode $z < z_d$, and $$q(K) = \sqrt{\kappa_0^2 - K^2} \quad (15)$$

with $\kappa_0$ being the wavenumber.

In a similar way to Eq. (5), the excitation intensity at a detector plane $z_d$ can be written as:

$$\tilde{U}_o(r_s, K_d; z_d) = S_0(R_s, z_s)\tilde{g}(R_s, K_d; z_s, z_d) \quad (16)$$

with $S_0$ being the source strength at $r_s$.

Using Eqs. (16) and (14) the normalized fluorescence expression for a given source position $r_s$ may be written as:

$$\frac{\tilde{U}_{fl}(R_s, K_d; z_s, z_d)}{\tilde{U}_0(R_s, K_d; z_s, z_d)} = \int_V \frac{g(R_s, R; z_s, z)\tilde{g}(R, K_d; z, z_d)}{\tilde{g}(R_s, K_d; z_s, z_d)} F(R, z) dR dz \quad (17)$$

By rewriting Eq. (17) as a summation, in a manner similar to that traditionally used in real space, the Hybrid expression for the weight matrix:

$$\tilde{U}_n(R_s, K_d; z_s, z_d) = \sum_{i=1}^{N} \tilde{W}(R_s, R_i, K_d; z_s, z_i, z_d) F(R_i, z_i) \quad (18)$$

where $\tilde{U}_n$ now represents the hybrid normalized data and W is the weight matrix:

$$\tilde{W}(R_s, R_i, K_d; z_s, z_i, z_d) = \left[ \frac{g(R_s, R_i; z_s, z_i)\tilde{g}(R_i, K_d; z_i, z_d) \Delta V}{\tilde{g}(R_s, K_d; z_s, z_d)} \right] \quad (19)$$

By substituting the expressions in Eq. (13), the weight matrix may be rewritten as:

$$\tilde{W}_{sd}^i = g(R_s, R_i; z_s, z_i) \exp(iq_0(K_d)(z_s - z_i)) \exp(iK_d(R_i - R_s)) \Delta V \quad (20)$$

The next step is to identify the cut-off frequency that provides optimal resolution. The spatial resolution at a distance L is found as follows. Given the diffusion length as:

$$L_d = \sqrt{D/\mu_a} \quad (21)$$

The full width at half maximum of the intensity generated by a point source at distance $L = z_s - z_d$ is then given by (Ripoll, J., M. Nieto-Vesperinas, et al. (1999). "Spatial resolution of diffuse photon density waves." J. Opt. Soc. Am. A 16: 1466-1476):

$$\Delta d = \frac{1}{2}\left(\left(\frac{1}{2\pi L_d} + \frac{\log(2)}{2\pi L}\right)^2 - \frac{1}{(2\pi L_d)^2}\right)^{-1/2} \quad (22)$$

Using this information, and given the relationship between the FWHM of a function to the FWHM of its Fourier Transform, one can select the Frequency Cut-off as a multiple of:

$$K_{max} = 4\pi\left(\left(\frac{1}{2\pi L_d} + \frac{\log(2)}{2\pi L}\right)^2 - \frac{1}{(2\pi L_d)^2}\right)^{1/2} \quad (23)$$

Figure 4:
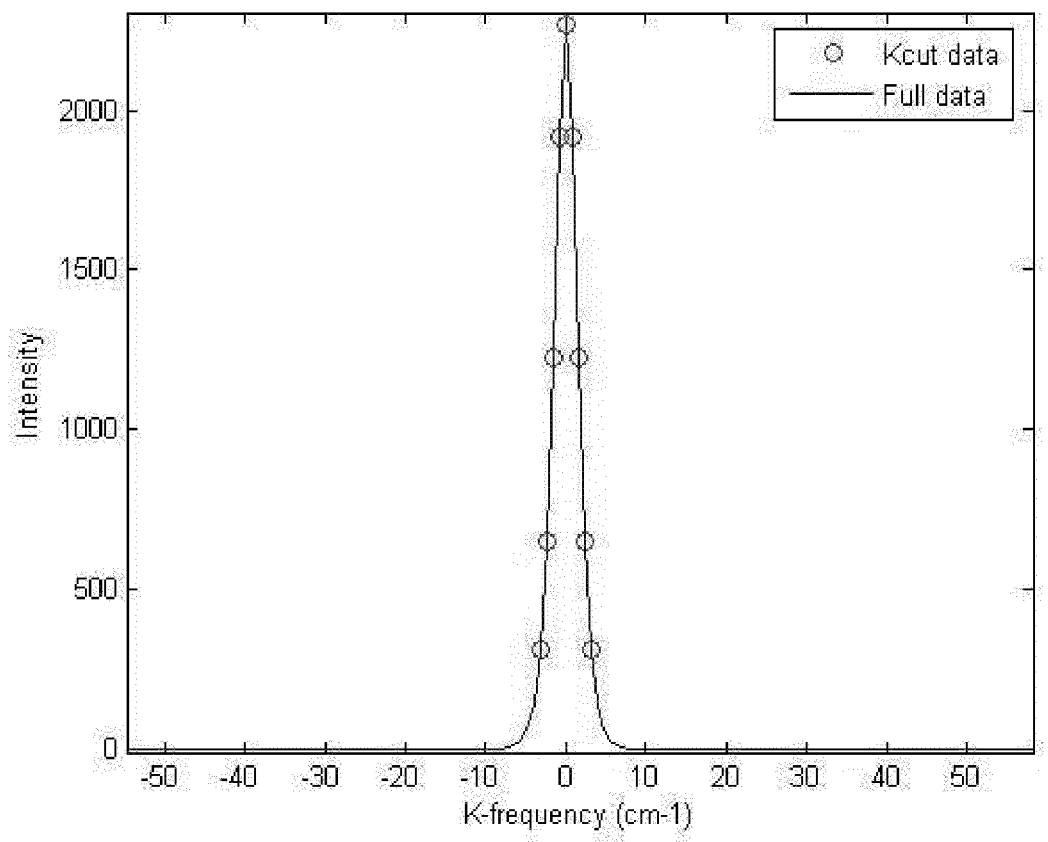
FIG. 4 is a graph showing the Fourier-space intensity profile of a full data set, with the discretized and cut-off components included in a hybrid reconstruction of an illustrative embodiment of the invention displayed as circles.

Typical values of the cut-off frequency lie in the range of $K_{cut} = K_{max}$ to $K_{cut} = 3K_{max}$ (FIGS. 3 and 4). Once the cut-off frequency has been selected, we will have a discretized subset of $N_K$ frequency values $K_i$. The matrix that needs to be inverted in this case would be:

$$[\tilde{W}_{s,i}^m]_{(N_s \times N_K) \times M} [F_m]_{M \times 1} = \left[ \frac{\tilde{U}_{fl}^i}{\tilde{U}_0^i} \right]_{(N_s \times N_K) \times 1} \quad (24)$$

where the subscript m, stands for the position of voxels m to be reconstructed for the fluorescence or the absorption, s stands for the $s^{th}$ source number, and i for the $i^{th}$ frequency $K_i$. The weight matrix W is hybrid, i.e. depends on the sources and voxels in real-space and on the detector data in Fourier space, thus this approach is termed the Hybrid approach.

In order to obtain a 3D reconstruction of fluorescent agent concentration, or of absorber concentration, the following equation is solved:

$$[F_m]_{1 \times M} = [\tilde{W}_{s,i}^m]^{-1}_{M \times (N_s \times N_K)} \frac{[\tilde{U}_{fl}^i]}{[\tilde{U}_0^i]} \quad (25)$$

There are several approaches that can be used to solve Eq. (25). Examples of approaches that could be used for solving for the concentration of fluorescent agent or absorbers, F are iterative approaches (such as the Algebraic Reconstruction Technique), Singular Value Approaches (Singular Value Decomposition, Tikhonoff Regularization, etc), and Gradient Methods, among others. Due to the decomposition of the measured data into its low frequency components, the size of the weight matrix W is several orders of magnitude smaller. For comparison purposes, a typical inversion problem would require in the order of $10^3$ voxels, use $10^2$ sources and need in the order of $10^3$ detectors. This means that the size of $W_{real}$ in real space would be of $10^3 \times 10^5$, i.e. $10^8$ elements. On the other hand, by using the Hybrid approach described herein, the weight matrix $W_{hybrid}$ would only need in the order of 25 frequencies, and thus have a size in the order of $10^3 \times 10^2 \times 25$, i.e. $10^6$ elements. Since computation speed is not proportional to size, but behaves non-linearly, this means that computationally intense problems in real space can be solved in seconds by using the hybrid approach, more importantly, still using small numbers of source measurements.

FIG. 2 is an illustrative block diagram of the steps of a method for obtaining a 3D map of an unknown fluorescing or absorbing probe, tissue, or other target object in a subject, according to an illustrative embodiment of the invention described herein. This block diagram compares the steps used in a preferred embodiment (e.g., a Hybrid Inversion approach 202) with those used in a conventional real-space imaging approach 204. Data from raw scan images produced by a fluorescence molecular tomography system at both excitation and emission wavelengths are input to the algorithm (205). Noise present in these images is handled via conventional thresholding (206). A boundary removal step 207 can be applied, optionally, as described in Eq. (8) and U.S. Patent Application No. 61/244,674, "Systems and Methods for Virtual Index-Matching of Diffusive Media," by Ripoll Lorenzo et al., the text of which is incorporated herein by reference in its entirety, in order to simplify the forward problem and alleviate the computational burden. Step 203 describes a decision point which may be optionally implemented to provide selection between hybrid (202) and conventional (204) inversions. In a conventional inversion (204), fluorescence data is normalized by emission data (Step 208) as described in U.S. Pat. No. 6,615,063, and U.S. Pat. No. 7,383,076, each entitled, "Fluorescence-Mediated Molecular Tomography," the texts of which are incorporated herein by reference in their entirety. The forward model computes a weight matrix (209) of Green's function expressions capturing every source-detector contribution, which is then inverted with a conventional inversion scheme such as Algebraic Reconstruction Technique (ART) run in real space (210) to produce a real vector of reconstructed fluorescence values (215). Alternatively, using the hybrid inversion approach 202, the thresholded detector data is Fourier-transformed (Step 211) and normalized by the excitation data (Step 212) as described in Equations (17) and (18). The consequent weight matrix of complex weights (Step 213) is computed as described in Equations (19), (20) and (24); the hybrid weight matrix 213 is then inverted with a complex-valued inversion scheme such as algebraic reconstruction (Step 214), resulting in a real-valued vector of reconstructed fluorescence values (215). Thus, a tomographic representation (e.g. image) of the fluorescent target object within the subject is obtained in real space.

FIG. 3 are images comparatively depicting the real-space intensity of a point source 302 and the absolute value of its Fourier transform 304 (top row). The bottom row shows the real 306 and imaginary components 308 of the Fourier detector data using Eq. (17), and illustrates the difference in data set size (512×512 versus 9×9) while still maintaining all the information.

FIG. 4 is a graph that displays the Fourier-space intensity profile of the full data, with the discretized and cut-off components included in a hybrid reconstruction according to an illustrative embodiment of the invention being displayed as circles.

Figure 5:
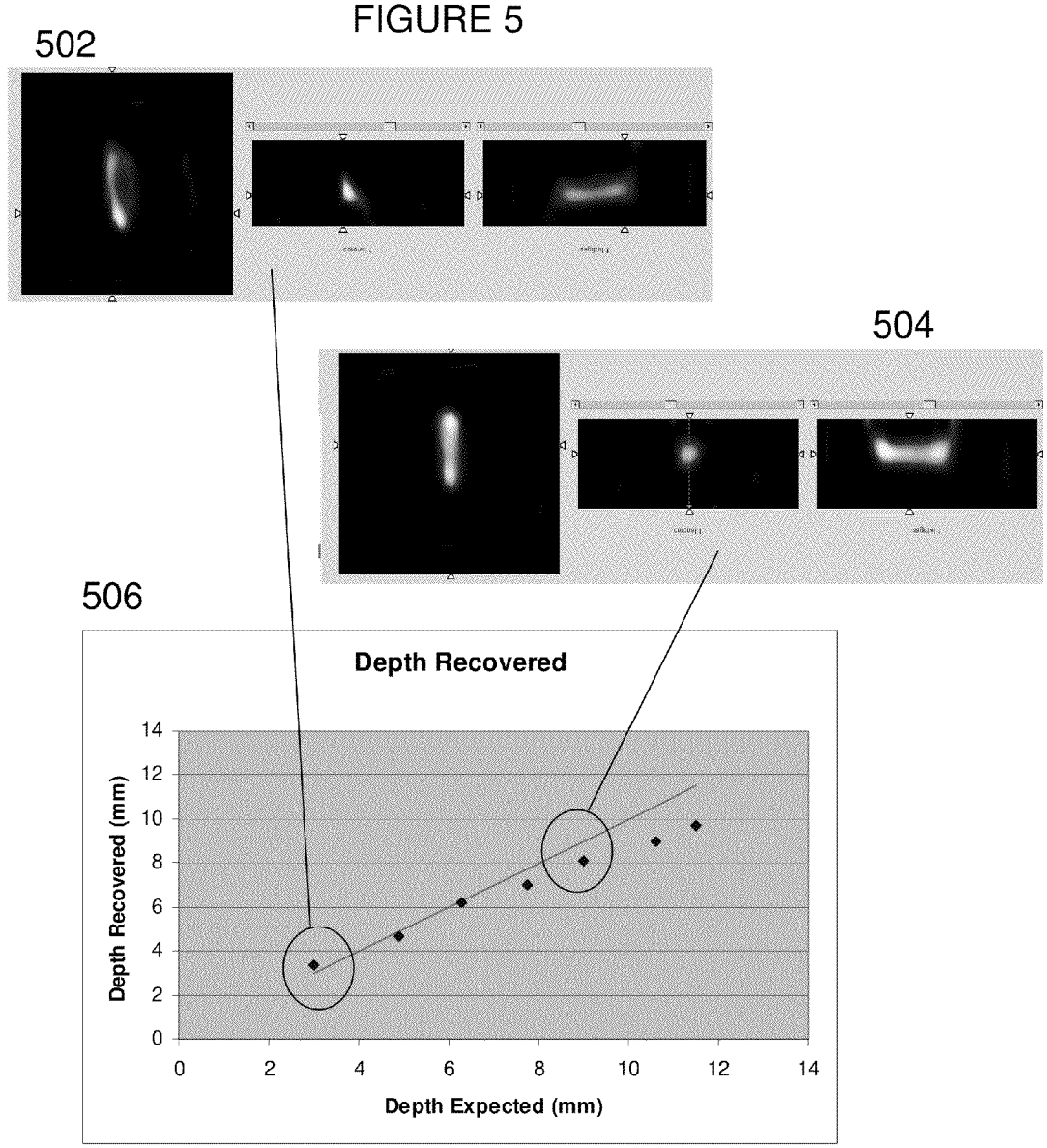
FIG. 5 is a schematic showing phantom reconstructions with a cylindrical fluorescent cavity at several depths, according to an illustrative embodiment of the invention.

FIG. 5 is a schematic 506 showing the depth recovery capability of the hybrid reconstruction approach according to an illustrative embodiment of the invention as a function of the expected values for a fluorescent tube embedded in a solid highly scattering phantom. The actual 3D reconstructions are shown with both top 502 and lateral 504 views.

Figure 6:
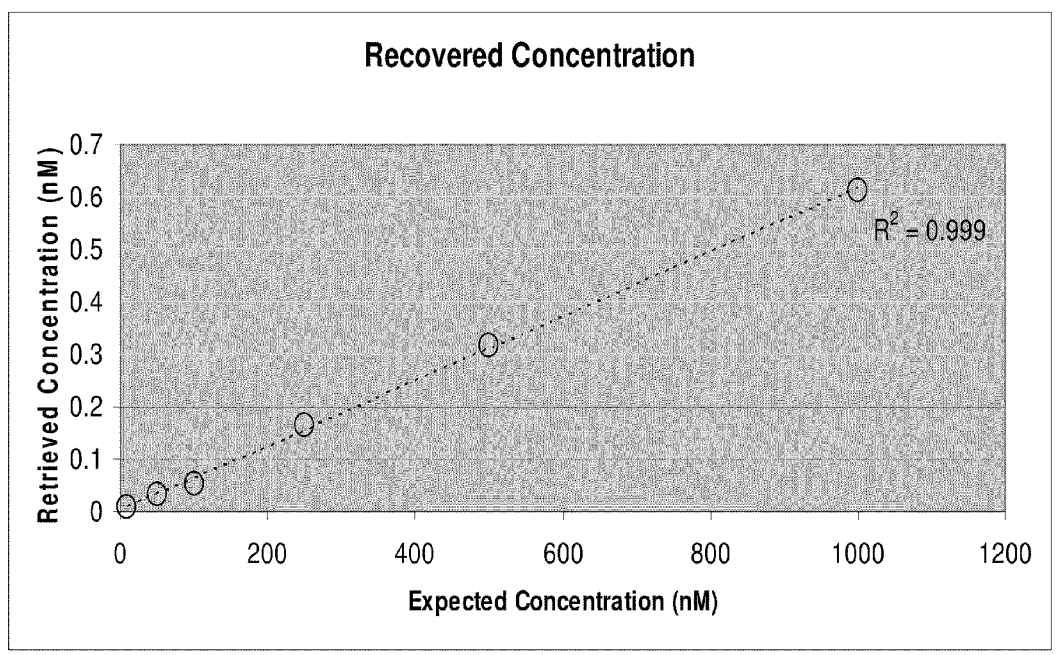
FIG. 6 is a graph illustrating the strong linearity of quantification in a hybrid reconstruction according to an illustrative embodiment of the invention.

FIG. 6 is a graph illustrating the quantification accuracy of a hybrid approach according to an illustrative embodiment of the invention. FIG. 6 shows the strong linearity of quantification in a hybrid reconstruction which enables robust calibration of such an approach. In all cases a Kcut of 2*Kmax was used. A total of 6 phantoms with different fluorophore concentrations placed in the middle of a 1.5 cm height phantom was used.

FIG. 7 is a schematic showing a hybrid in vivo tomographic reconstruction of an animal according to an illustrative embodiment of the invention, where the animal has been injected with fluorescent agent in a 4T-1 cancer model.

Figure 8:
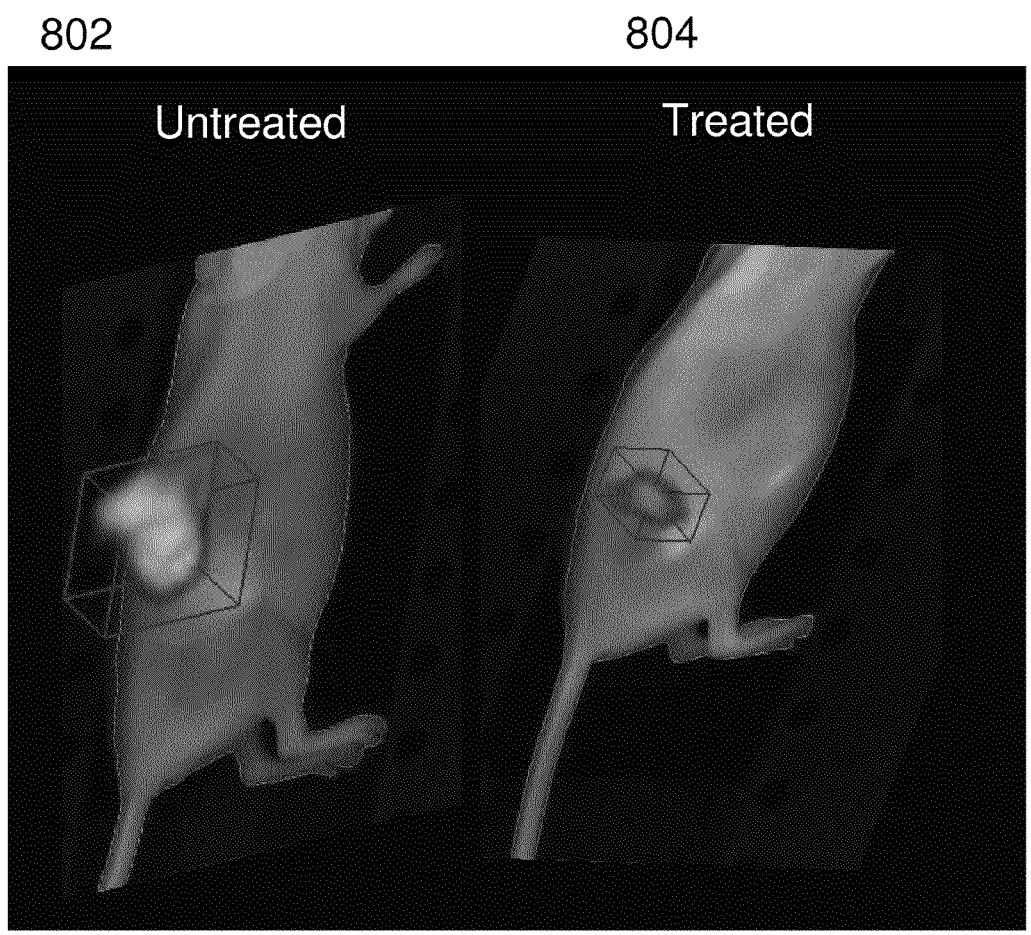
FIG. 8 is a schematic showing comparative volume renderings of treated and untreated tumor-bearing animals reconstructed with a hybrid reconstruction approach, according to an illustrative embodiment of the invention.

FIG. 8 is a schematic showing another hybrid in vivo tomographic reconstruction of an animal according to an illustrative embodiment of the invention, where the animal has been injected with another fluorescent agent in a 4T-1 cancer model, with the left image showing an untreated tumor 802 and the right image showing a treated tumor 804.

Illustrative examples of tomographic reconstructions performed with the benefit of the present invention are shown in FIGS. 5-8. FIG. 5 shows phantom reconstructions with a cylindrical fluorescent cavity at several depths; FIG. 6 shows the strong linearity of quantification in a hybrid reconstruction which enables robust calibration of such an approach; FIG. 7 shows a volume rendering of an in vivo dataset from a tumor-bearing mouse injected with a fluorescent contrast agent; FIG. 8 similarly displays comparative volume renderings of treated 804 and untreated 802 tumor-bearing animals reconstructed with a hybrid reconstruction approach.

In certain embodiments, the methods of the present invention are useful with optical imaging modalities and measurement techniques including, but not limited to: endoscopy; fluorescence endoscopy; luminescence imaging; bioluminescence tomography, time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

Commercially available systems that can be used to employ the methods described herein include, but are not limited to, the following: eXplore Optix™, Optix® and SoftScan® (ART—Advanced Research Technologies, Canada), NightOWL® II LB (Berthold Technologies, Germany), NanoSPECT™, NanoPET/CT™ and HiSPECT® (Bioscan, Washington, DC), Photon Imager™, Beta Imager™, Micro Imager, Gamma Imager (Biospace Lab, France), Maestro® FLEX and Nuance® FLEX (Cambridge Research and Instrumentation—Cri®, Woburn, Mass.), LightSpeed™, BrightSpeed™ and MR Signa® Series, eXplore Series, Triumph™ (GE® Healthcare, United Kingdom), Kodak® In-Vivo Imaging FX Systems, Kodak® In-Vivo Multispectral Imaging FX Systems and Kodak® Image Station 4000 series (KODAK® and Carestream®, Rochester, N.Y.), Aquacosmos® (Hamamatsu, Japan), CTLM® and LILA Imaging Systems (Imaging Diagnostic Systems—IMDS, Plantation, Fla.), Odyssey® Infrared Imaging System, Pearl® Imager (LI-COR, Lincoln, Nebr.), IMRIS® Neuro System (IMRIS®, Canada), Cellvizio® (Mauna Kea Technologies, France), SPY® and SPY®-TMR Systems, HELIOS™ LUNA™, PINPOINT®, and OPTTX® Imaging Systems (Novadaq, Canada), DYNOT Imaging System (NIRx, Glen Head, N.Y.), OV100 and IV100 (Olympus Corporation, Japan), Lumazone® (Photometrics, Tucson, Ariz.), and IVIS® Systems, IVIS® 3D, IVIS® Kinetics, IVIS® Spectrum and IVIS® Lumina (Xenogen®, Alamaeda, Calif. and Caliper® Life Sciences, Hopkinton, Mass.), iBox® (UVP, Upland, Calif.), and VisEn FMT-1, VisEn FMT 1500™, and VisEn FMT 2500™ LX (VisEn™ Medical, Bedford, Mass.).

Systems of the invention may include a computer which executes software that controls the operation of one or more instruments, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer is preferably a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the instrument (e.g., displaying a tomographic image), a keyboard for enabling the operator to enter information and commands, and/or a printer for providing a print-out, or permanent record, of measurements made by the system and for printing diagnostic results, for example, for inclusion in the chart of a patient. In certain embodiments, some commands entered at the keyboard enable a user to perform certain data processing tasks. In certain embodiments, data acquisition and data processing are automated and require little or no user input after initializing the system.

In certain embodiments, the invention features an in vivo imaging method for selectively imaging a subject containing two or more imaging probes simultaneously, wherein two or more imaging probes are administered to a subject, either at the same time or sequentially. The imaging probes can be any combination of optical or other imaging agents. A single imaging agent may serve as both an optical and other imaging modality agent, e.g., dual imaging agent. The method therefore allows the recording of multiple biological processes, functions or targets. The methods of the invention can be used to determine a number of indicia, including tracking the localization of the imaging probes in the subject over time or assessing changes or alterations in the metabolism and/or excretion of the imaging probes in the subject over time. The methods can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

In certain embodiments, this invention can be used with other imaging approaches such as the use of devices including but not limited to various scopes (microscopes, endoscopes), catheters and optical imaging equipment, for example computer based hardware for tomographic presentations.

The invention can be used to help a physician, surgeon, or other medical personnel to identify and characterize areas of disease, such as arthritis, cancers, metastases or vulnerable or unstable plaque, to distinguish diseased and normal tissue, such as detecting tumor margins that are difficult to detect.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies. The methods of the invention can also be used in prognosis of a disease or disease condition. With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone, including metastases), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosus, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants). The methods of the invention can therefore be used, for example, to determine the presence of tumor cells and localization and metastases of tumor cells, the presence and localization of inflammation, including the presence of activated macrophages, for instance in atherosclerosis or arthritis, the presence and localization of vascular disease including areas at risk for acute occlusion (e.g., vulnerable plaques) in coronary and peripheral arteries, regions of expanding aneurysms, unstable plaque in carotid arteries, and ischemic areas, and stent thrombosis. The methods and compositions of the invention can also be used in identification and evaluation of cell death, injury, apoptosis, necrosis, hypoxia and angiogenesis. The methods and compositions of the invention can also be used in for monitoring trafficking and localization of certain cell types, including T-cells, tumor cells, immune cells, stem cells, and other cell types. In particular, this method may be used to monitor cell based therapies. The methods and compositions of the invention can also be used as part of photodynamic therapy, including imaging, photoactivation and therapy monitoring.

In certain embodiments, the systems and methods described herein can be used to image endogenous fluorescence in a subject. For example, a gene encoding a fluorescent protein, such as green, red or infrared fluorescent protein, can be included adjacent to a gene of interest that is to be expressed in an animal or human subject using standard gene therapy and transgenic techniques. The expression of the gene of interest can be determined indirectly by imaging the fluorescent protein. If this protein is expressed, then the gene of interest has also been expressed. Fluorescence properties of endogenous fluorescent proteins are described in Giepmans et al., *Science,* 312: 217-224, 2006; Shaner et al., *Nature Methods* 2:905-909, 2005; and Zhang et al., *Nat. Rev. Mol. Biol.* 3: 906-918, 2002; Ai et al., *Biochemistry* 46:5904-5910, 2007; Shaner et al., *Nat. Biotech* 22:1567-1572, 2004; Campbell et al., *Proc. Nat. Acad. Sci.* 99:7877-7882, 2002; Heikal et al. *Proc. Nat. Acad. Sci.* 97:11996-12001, 2000; Baird et al., *Proc. Nat. Acad. Sci.* 97:11984-11989, 2000; Tsien, *Ann. Rev. Biochem.* 67:509-44, 1998; Heim et al., *Curr. Biol.* 6:178-182, 1996; Cubitt et al., *Trends Biochem Sci.* 11:448-455, 1995; Heim et al., *Proc. Nat. Acad. Sci* 91:12501-12504, 1994; the relevant text incorporated by reference herein.

Imaging Probes

The imaging system and method can be used with a number of different imaging probes, for example, (1) probes that become activated after target contact (e.g., binding or interaction) (Weissleder et al., *Nature Biotech.,* 17:375-378, 1999; Bremer et al., *Nature Med.,* 7:743-748, 2001; Campo et al., *Photochem. Photobiol.* 83:958-965, 2007); (2) wavelength shifting beacons (Tyagi et al., *Nat. Biotechnol.,* 18:1191-1196, 2000); (3) multicolor (e.g., fluorescent) probes (Tyagi et al., *Nat. Biotechnol.,* 16:49-53, 1998); (4) probes that have high binding affinity to targets, e.g., that remain within a target region while non-specific probes are cleared from the body (Achilefu et al., *Invest. Radiol.,* 35:479-485, 2000; Becker et al., *Nature Biotech.* 19:327-331, 2001; Bujai et al., *J. Biomed. Opt.* 6:122-133, 2001; Ballou et al. *Biotechnol.*

*Prog.* 13:649-658, 1997; and Neri et al., *Nature Biotech.* 15:1271-1275, 1997); (5) quantum dot or nanoparticle-based imaging probes, including multivalent imaging probes, and fluorescent quantum dots such as amine T2 MP EviTags® (Evident Technologies) or Qdot® Nanocrystals (Invitrogen™); (6) non-specific imaging probes e.g., indocyanine green, AngioSense® (VisEn Medical); (7) labeled cells (e.g., such as cells labeled using exogenous fluorophores such as VivoTag™ 680, nanoparticles, or quantum dots, or by genetically manipulating cells to express fluorescent or luminescent proteins such as green or red fluorescent protein; and/or (8) X-ray, MR, ultrasound, PET or SPECT contrast agents such as gadolinium, metal oxide nanoparticles, X-ray contrast agents including iodine based imaging agents, or radioisotopic form of metals such as copper, gallium, indium, technetium, yttrium, and lutetium including, without limitation, 99m-Tc, 111-In, 64-Cu, 67-Ga, 186-Re, 188-Re, 153-Sm, 177-Lu, and 67-Cu. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this invention, the imaging probes can be administered systemically or locally by injecting an imaging probe or by topical or other local administration routes, such as "spraying".

Furthermore, imaging probes used in the application of this invention can be conjugated to molecules capable of eliciting photodynamic therapy. These include, but are not limited to, Photofrin, Lutrin, Antrin, aminolevulinic acid, hypericin, benzoporphyrin derivative, and select porphyrins.

In general, fluorescent quantum dots used in the practice of this invention are nanocrystals containing several atoms of a semiconductor material (including but not limited to those containing cadmium and selenium, sulfide, or tellurium; zinc sulfide, indium-antimony, lead selenide, gallium arsenide, and silica or ormosil), which have been coated with zinc sulfide to improve the properties of the fluorescent agents.

In particular, molecular imaging probes are a preferred type of imaging probe. A molecular imaging probe is a probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by imaging probes include, for example, antibodies, proteins, glycoproteins, cell receptors, neurotransmitters, integrins, growth factors, cytokines, lymphokines, lectins, selectins, toxins, carbohydrates, internalizing receptors, enzyme, proteases, viruses, microorganisms, and bacteria.

In certain embodiments, optical imaging probes have excitation and emission wavelengths in the red and near infrared spectrum in the range 550-1300 or 400-1300 nm or about 440 and about 1100 nm, between about 550 and about 800 nm, between about 600 and about 900 nm. Use of this portion of the electromagnetic spectrum maximizes tissue penetration and minimizes absorption by physiologically abundant absorbers such as hemoglobin (<650 nm) and water (>1200 nm). Optical imaging probes with excitation and emission wavelengths in other spectrums, such as the visible and ultraviolet light spectrum, can also be employed in the methods of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); U.S. Pat. No. 7,445,767 to Licha, et al. (2008); U.S. Pat. No. 6,534,041 to Licha et al. (2003); U.S. Pat. No. 7,547,721 to Miwa et al. (2009); U.S. Pat. No. 7,488,468 to Miwa et al. (2009); U.S. Pat. No. 7,473,415 to Kawakami et al. (2003); also WO 96/17628, EP 0 796 111 B1, EP 1 181 940 B1, EP 0 988 060 B1, WO 98/47538, WO 00/16810, EP 1 113 822 B1, WO 01/43781, EP 1 237 583 A1, WO 03/074091, EP 1 480 683 B1, WO 06/072580, EP 1 833 513 A1, EP 1 679 082 A1 WO 97/40104, WO 99/51702, WO 01/21624, and EP 1 065 250 A1; and Tetrahedron Letters 41, 9185-88 (2000).

Exemplary fluorochromes for optical imaging probes include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™680, VivoTag™-5680, VivoTag™-5750 (VIsEN Medical); Dy677, Dy682, Dy752 and Dy780 (Dyomics®); DyLight® 547, and/or DyLight® 647 (Pierce); HiLyte Fluor™ 647, HiLyte Fluor™ 680, and HiLyte Fluor™ 750 (AnaSpec®); IRDye® 800CW, IRDye® 800RS, and IRDye® 700DX (Li-Cor®); ADS780WS, ADS830WS, and ADS832WS (American Dye Source); XenoLight CF™ 680, XenoLight CF™ 750, XenoLight CF™ 770, and XenoLight DiR (Caliper® Life Sciences); and Kodak® X-SIGHT® 650, Kodak® X-SIGHT 691, Kodak® X-SIGHT 751 (Carestream® Health).

The text of all references identified herein are incorporated by reference herein in their entirety.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A fluorescence molecular tomography imaging system comprising:
   an excitation light source;
   an optical imaging apparatus configured to direct light from the excitation light source into a subject at a plurality of locations;
   a detector configured to detect at multiple locations fluorescent light emanating from a region of the subject; and
   a processor configured to process data corresponding to the detected fluorescent light emanating from the region of the subject to produce a tomographic representation of the region of the subject, wherein the processor is configured to execute instructions to:
   (a) establish a forward model of excitation light propagation from the excitation light source to the region of the subject and of fluorescent light propagation from the region to the detector using the data corresponding to the detected fluorescent light, wherein:
   (i) the excitation light source is represented in real space
   (ii) the detected fluorescent light is represented in frequency space,
   (iii) in the forward model, boundary removal equations are used to convert data corresponding to the surface of the subject into a simulated infinite homogeneous medium, and
   (iv) the forward model is established as a discretized weight matrix of normalized elements; and
(b) invert the weight matrix to obtain the tomographic representation of the region of the subject in real space.

2. The system of claim 1, wherein the detector is further configured to detect at multiple locations excitation light emanating from the subject, and wherein the processor is configured to execute instructions to establish the forward model using the data corresponding to the detected excitation light and the detected fluorescent light wherein the detected excitation light and the detected fluorescent light are represented in frequency space.

3. The system of claim 1, wherein, in the forward model, a surface of the subject is identified and boundary conditions are established for the surface.

4. The system of claim 1, wherein the data corresponding to the surface of the subject comprises an experimental measurement of surface flux distribution.

5. The system of claim 1, wherein the detected fluorescent light is emitted from a probe within the region of the subject, and the forward model in (a) models excitation light propagation from the excitation light source to the probe and emitted fluorescent light propagation from the probe to the detector.

6. The system of claim 5, wherein, in the forward model, a Born approximation is used to express an intensity of the detected fluorescent light emitted from the probe having spatially-varying concentration within the region.

7. The system of claim 6, wherein the intensity of the detected fluorescent light is normalized using an intensity of spatially-corresponding detected excitation light.

8. The system of claim 2, wherein the forward model in (a) represents the detected excitation light and the detected fluorescent light in Fourier space.

9. The system of claim 1, wherein the excitation light source or the optical imaging apparatus comprises a scanner configured to direct light into the subject at a plurality of locations, thereby defining a plurality of source locations.

10. The system of claim 9, wherein the plurality of source locations are non-uniformly spaced.

11. The system of claim 1, wherein the detector comprises an array of detector locations, and wherein the forward model in (a) is established using data obtained from the array of detector locations.

12. The system of claim 11, wherein there are substantially more detector locations than source locations.

13. The system of claim 1, wherein the excitation light has wavelength within a range from about 500 nanometers to about 1000 nanometers.

14. The system of claim 1, wherein the excitation light comprises at least one member selected from the group consisting of continuous wave light, time-resolved light, and intensity modulated light.

15. The system of claim 1, wherein the forward model in (a) models excitation light propagation from the excitation light source to the region of the subject and fluorescent light propagation from the region to the detector, where there is free space between the surface of the subject and the detector.

16. A method of imaging a distribution of a fluorescent probe within a region of a subject, the method comprising the steps:
   (a) administering to the subject a probe comprising a red or near-infrared fluorophore;
   (b) directing near-infrared excitation light into the subject at multiple locations to transilluminate through or reflect from the region of the subject;
   (c) detecting fluorescent light emitted from the probe within the region of the subject; and
   (d) processing data corresponding to the detected fluorescent light and, the detected excitation light, to provide a tomographic representation of the region of the subject, wherein the processing step comprises:
      (i) establishing a forward model of excitation light propagation from an excitation light source to the probe within the region of the subject and of emission light propagation from the probe to a detector using the data corresponding to the detected fluorescent light and, the detected excitation light, wherein:
         (A) a surface of the subject is identified and boundary conditions are established for the surface, or, alternatively, boundary removal equations are used to convert data corresponding to the surface of the subject into a simulated infinite homogeneous medium;
         (B) the excitation light source is represented in real space;
         (C) the detected fluorescent light and, the detected excitation light, is represented in frequency space; and
         (D) the forward model is established as a discretized weight matrix of normalized elements; and
      (ii) inverting the weight matrix to obtain the tomographic representation of the region of the subject in real space.

17. The method of claim 16, wherein the tomographic representation comprises a map of concentration of the probe within the region of the subject.

18. The method of claim 16, wherein the tomographic representation indicates an area of disease such as arthritis, cancer, metastasis, plaque, or a combination of two or more of the foregoing, within the region of the subject.

19. The method of claim 16, wherein the tomographic representation indicates a boundary of a tumor within the region of the subject.

20. The method of claim 16, wherein the probe is an endogenous probe.

21. The method of claim 16, wherein the probe comprises a member selected from the group consisting of a molecular probe, a fluorescent molecular probe, an activatable fluorescent probe, an enzyme-activatable fluorescent probe, a targeted fluorescent probe, a red or near-infrared fluorescent molecular probe, a fluorescent protein, a fluorescent biomolecule, a non-specific fluorescent probe, quantum dots, a receptor-targeted near-infrared fluorochrome, an antibody- or antibody-like targeted red or near-infrared fluorochrome, a wavelength-shifting beacon, a multi-color fluorescence probe, and a lanthanide metal-ligand probe.

22. The method of claim 16, wherein step (a) comprises administering to the subject a plurality of probes having optically distinguishable fluorescent emission wavelengths, step (c) comprises detecting fluorescent light emitted from each of the probes, and step (d) comprises processing data corresponding to the detected light to provide one or more tomographic representations.

23. The method of claim 16, further comprising the step of determining an effect of the probe on the region within the object using the tomographic representation.

24. The method of claim 16, further comprising, prior to step (d), (c2) detecting excitation light transmitted through or reflected from the region of the subject.

25. The method of claim 16, further comprising the step of imaging at excitation and emission wavelengths of a natural tissue chromophore.

26. The method of claim 16, wherein the tomographic representation comprises a map showing quantity of the probe in three dimensions.

27. The method of claim 16, wherein the tomographic representation comprises one or more images, and wherein the method further comprises storing the one or more images, displaying the one or more images, or both storing and displaying the one or more images.

28. The method of claim 16, wherein the tomographic representation comprises a three-dimensional tomographic image and wherein the method further comprises the step of combining the three-dimensional tomographic image with magnetic resonance, x-ray computed tomography, bioluminescence tomography, spectroscopy, ultrasound, single photon emission tomography, or positron emission tomography imaging data.

29. The method of claim 16, further comprising the step of detecting or monitoring a cellular abnormality or disease using the tomographic representation, wherein the cellular abnormality or disease comprises at least one member selected from the group consisting of inflammation, cancer, cardiovascular disease, respiratory disease, dermatologic disease, ophthalmic disease, infectious disease, immunologic disease, central nervous system disease, inherited diseases, metabolic diseases, environmental diseases, bone-related disease, neurodegenerative disease, and surgery-related complications.

30. The method of claim 16, wherein the subject is a mammal.

31. The method of claim 16, wherein the probe comprises an endogenous fluorophore that is encoded by a gene within the subject.

32. An apparatus for reconstructing a tomographic representation of a probe within a region of a subject, the apparatus comprising:
  a memory that stores code defining a set of instructions; and
  a processor that executes the instructions thereby to:
  (a) establish a forward model of excitation light propagation from an excitation light source to the probe within the region of the subject and of emission light propagation from the probe to a detector using data corresponding to detected fluorescent light, wherein:
    (i) a surface of the subject is identified and at least one step selected from (A) and (B) is performed: (A) boundary conditions are established for the surface, and (B) boundary removal equations are used to convert data corresponding to the surface of the subject into a simulated infinite homogeneous medium, thereby simplifying the forward model;
    (ii) the excitation light source is represented in real space;
    (iii) the detected fluorescent light is represented in frequency space; and
    (iv) the forward model is established as a discretized weight matrix of normalized elements; and
  (b) invert the weight matrix to obtain the tomographic representation of the region of the subject in real space.

33. The apparatus of claim 32, wherein the processor executes the instructions to establish the forward model using data corresponding to detected excitation light and the detected fluorescent light, wherein the detected fluorescent light and the detected excitation light are represented in frequency space.

34. A diffuse optical tomography imaging system comprising:
  one or more illumination sources;
  an optical imaging apparatus configured to direct light from the at least one illumination source into a subject at a plurality of locations;
  a detector configured to detect at multiple locations light emanating from the subject to obtain a first and a second measurement, wherein the first measurement is a reference measurement and the second measurement corresponds to absorption of at least a portion of the illuminating light as it passes through a light-absorbing region within the subject, and wherein the reference measurement does not reflect all of said absorption; and
  a processor configured to process data corresponding to the first and second measurements of detected light emanating from the subject, wherein the processor is configured to execute instructions to:
  (a) establish a forward model of light propagation from at least one of the one or more illumination sources to the light-absorbing region within the subject and of light propagation from the region to the detector using the data corresponding to the first and second measurements, wherein:
    (i) the at least one illumination source is represented in real space;
    (ii) the detected light is represented in frequency space;
    (iii) in the forward model, boundary removal equations are used to convert data corresponding to the surface of the subject into a simulated infinite homogeneous medium; and
    (iv) the forward model is established as a discretized weight matrix of normalized elements; and
  (b) invert the weight matrix to obtain the tomographic representation of the region of the subject in real space.

35. The method of claim 24, wherein at least steps (b), (c), (c2), and (d) are repeated to obtain tomographic representations as a function of time.

36. The method of claim 35, further comprising:
  (i) the step of monitoring kinetics of a distribution of the probe within the region using the tomographic representations, or
  (ii) the step of monitoring kinetics of activation of the probe using the tomographic representations.

37. A non-transitory computer readable medium storing instructions thereon, wherein the instructions, when executed, cause a processor to produce a tomographic representation of a region of a subject by:
  receiving data corresponding to detected fluorescent light emanating from the region of the subject, wherein
    the data is provided by a detector configured to detect at multiple locations fluorescent light emanating from a region of the subject, wherein
    the fluorescent light emanates from the region of the subject responsive to excitation light directed from an excitation light source by an optical imaging apparatus into the subject at a plurality of locations;

establishing a forward model of excitation light propagation from the excitation light source to the region of the subject and of fluorescent light propagation from the region to a detector location of the detector using the data corresponding to the detected fluorescent light, wherein:

(i) the excitation light source is represented in real space, (ii) the detected fluorescent light is represented in frequency space, (iii) in the forward model, boundary removal equations are used to convert data corresponding to the surface of the subject into a simulated infinite homogeneous medium, and (iv) the forward model is established as a discretized weight matrix of normalized elements; and inverting the discretized weight matrix to obtain the tomographic representation of the region of the subject, wherein the tomographic representation is in real space.

* * * * *